(12) United States Patent
Blumberg et al.

(10) Patent No.: US 9,277,748 B2
(45) Date of Patent: Mar. 8, 2016

(54) AGONIST/ANTAGONIST COMPOSITIONS AND METHODS OF USE

(75) Inventors: Peter M. Blumberg, Frederick, MD (US); Larry V. Pearce, Rockville, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days.

(21) Appl. No.: 13/634,447

(22) PCT Filed: Mar. 11, 2011

(86) PCT No.: PCT/US2011/028132
§ 371 (c)(1),
(2), (4) Date: Apr. 25, 2013

(87) PCT Pub. No.: WO2011/112956
PCT Pub. Date: Sep. 15, 2011

(65) Prior Publication Data
US 2013/0203736 A1 Aug. 8, 2013

Related U.S. Application Data

(60) Provisional application No. 61/340,063, filed on Mar. 12, 2010.

(51) Int. Cl.
| | | |
|---|---|---|
| A61K 31/55 | (2006.01) | |
| A01N 43/46 | (2006.01) | |
| A61K 31/165 | (2006.01) | |
| A61K 31/4468 | (2006.01) | |
| A61K 31/5375 | (2006.01) | |
| A61K 36/81 | (2006.01) | |
| A61K 45/06 | (2006.01) | |
| A01N 37/18 | (2006.01) | |

(52) U.S. Cl.
CPC ............... *A01N 43/46* (2013.01); *A01N 37/18* (2013.01); *A61K 31/165* (2013.01); *A61K 31/4468* (2013.01); *A61K 31/5375* (2013.01); *A61K 31/55* (2013.01); *A61K 36/81* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,951,070 B2 * | 10/2005 | Fleischhauer et al. | 42/1.08 |
| 6,957,750 B1 | 10/2005 | Trudell | |
| 7,270,802 B2 * | 9/2007 | Loghman-Adham | 424/45 |
| 7,304,059 B2 * | 12/2007 | Bakthavatchalam et al. | 514/233.8 |
| 8,318,728 B2 * | 11/2012 | Chong | A61K 31/4188 514/227.8 |
| 2004/0126323 A1 | 7/2004 | Shevchuk et al. | |
| 2004/0142958 A1 | 7/2004 | Herzberg et al. | |
| 2006/0198806 A1 * | 9/2006 | Reilly | 424/70.13 |

FOREIGN PATENT DOCUMENTS

| | | | | |
|---|---|---|---|---|
| GB | WO 2008104738 A1 * | 9/2008 | | A61K 9/08 |
| WO | 9004965 A1 | 5/1990 | | |
| WO | 9820867 A1 | 5/1998 | | |
| WO | WO 98/20867 * | 5/1998 | | |
| WO | 0158447 A1 | 8/2001 | | |
| WO | 2004062641 A1 | 7/2004 | | |
| WO | 2005032555 A2 | 4/2005 | | |
| WO | 2008104738 A1 | 9/2008 | | |
| WO | 2009116084 A2 | 9/2009 | | |

OTHER PUBLICATIONS

Reilly, C. et al., J Biochem Mol Toxicol. 2005; 19 (4): 266-275.*

* cited by examiner

*Primary Examiner* — Alicia L Otton
*Assistant Examiner* — Jeanmarie Calvillo
(74) *Attorney, Agent, or Firm* — Bryan D. Zerhusen; Locke Lord LLP

(57) ABSTRACT

The present invention relates to novel compositions comprising an agonist and an antagonist, in certain ratios which allow for the onset of agonist action followed quickly by alleviation by antagonist action, and methods of use in personal defense and law enforcement.

20 Claims, 18 Drawing Sheets

FIG. 1

Improved spray for repellency and incapacitation of people and animals
Structures of capsaicin (agonist) and the five antagonists used in the examples provided.

1) capsaicin

2) BCTC

3) IodoRTX

4) JYL-827

5) AMG9810

6) capsazepine

Experiments were conducted with 300 nM capsaicin plus the indicated concentrations of the antagonists. Curves are the mean from three independent experiments.

Series of calcium imaging curves for BCTC

- 300 CAP
- 300 + 1 nM BCTC
- 300 + 10 nM BCTC
- 300 + 30 nM BCTC
- 300 + 100 nM BCTC

Series of calcium imaging curves for 5' I-RTX

- 300 CAP
- 300 + 1 nM I-RIX
- 300 + 10 nM I-RIX
- 300 + 30 nM I-RIX
- 300 + 300 nM I-RIX

Series of calcium imaging curves for JYL-827

▨ 300 CAP
■ 300 + 3 nM JYL-827
▩ 300 + 30 nM JYL-827
▨ 300 + 100 nM JYL-827
▨ 300 + 300 nM JYL-827

Series of calcium imaging curves for AMG9810

▨ 300 CAP
■ 300 + 10 nM AMG 9810
▩ 300 + 100 nM AMG 9810
▨ 300 + 300 nM AMG 9810
▨ 300 + 1000 nM AMG 9810
☐ 300 + 3000 nM AMG 9810

Series of calcium imaging curves for capsazepine

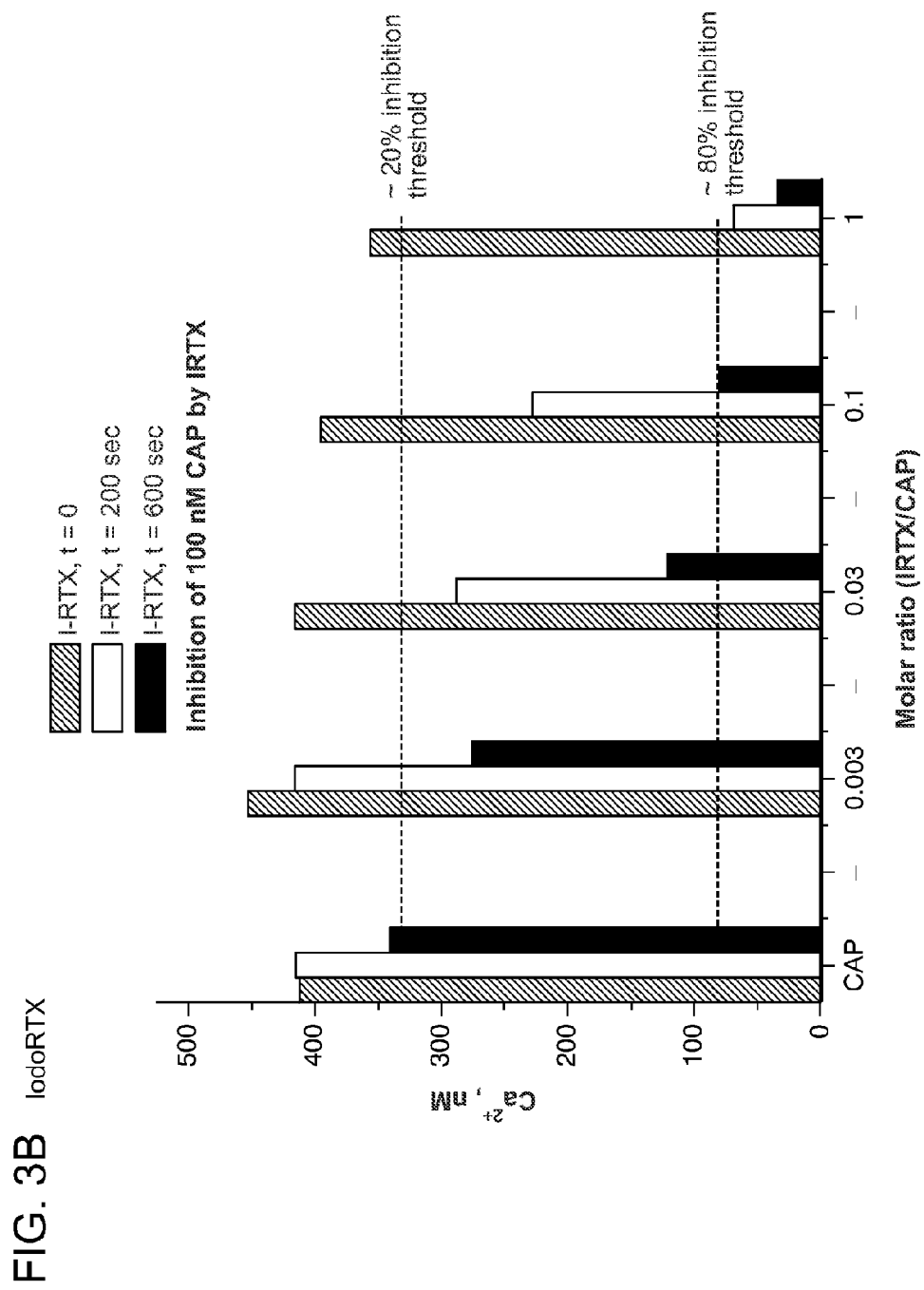
FIG. 3B IodoRTX

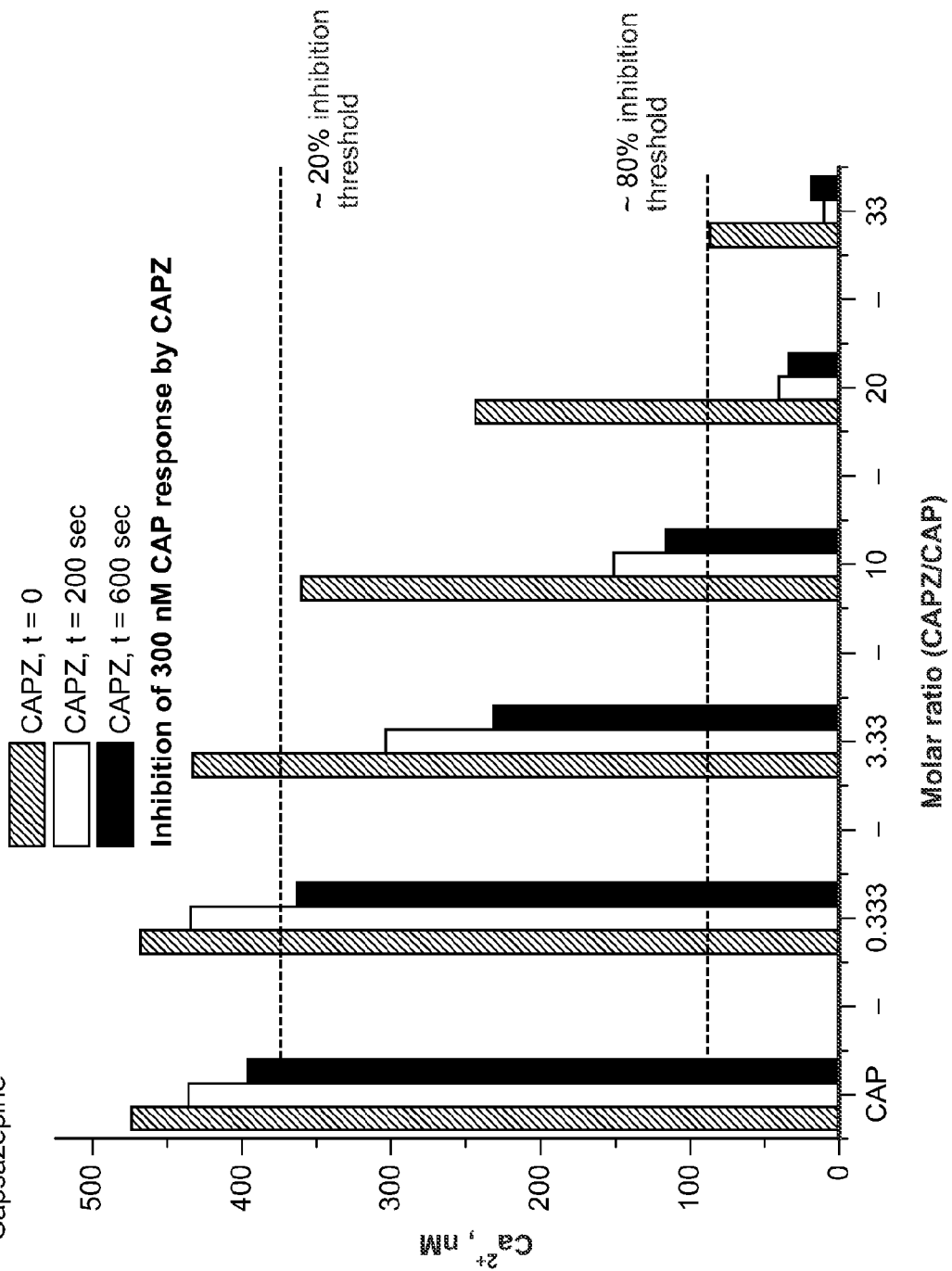
FIG. 3E Capsazepine

AGONIST/ANTAGONIST COMPOSITIONS AND METHODS OF USE

RELATED APPLICATIONS

This application is a 35 U.S.C. §371 U.S. national entry of International Application PCT/US2011/028132 (WO 2011/112956) having an International filing date of Mar. 11, 2011, which claims the benefit of U.S. provisional application 61/340,063, filed Mar. 12, 2010, the contents of which are incorporated herein in their entirety by reference.

STATEMENT OF GOVERNMENT INTEREST

This invention was funded by the National Cancer Institute at the National Institutes of Health. The United States Government has certain rights in this invention.

TECHNICAL FIELD

The present invention relates to novel compositions comprising a fast acting agonist and a slow acting antagonist, in certain ratios which allows for the onset of agonist action followed quickly by alleviation by antagonist action, and methods of use.

BACKGROUND OF THE INVENTION

Non-lethal weapons are designed to incapacitate the target, and when properly used do not result in any injuries, fatalities or after effects. Non-lethal weapons in the form of aerosol sprays capable of temporarily incapacitating a target have shown great use both for enforcement and defensive purposes. These non-lethal sprays are particularly useful in close proximity encounters, such as breaking up a bar fight or intervening in a domestic disturbance; stopping fleeing suspects; in hostage or terrorist situations; in barricade situations, where the subject is violent, but has not taken a hostage; and generally in crowd control or riot situations.

Aerosol sprays commercially available are of three types: chloroacetophenone (CN) commonly known as mace, orthochlorobenzylidenemalononitrile (CS) commonly known as tear gas, and oleoresin capsicum (OC) also known as pepper spray. Both mace and tear gas are lachrymators that cause tearing and irritation. However, they have no effect on those who are enraged or are under the influence of narcotics, or alcohol. Pepper sprays contain an extract of hot pepper and act as an inflammatory agent causing closing of the eyes and coughing Initial aerosol type formulations were of the lachrymator type, such as Chemical Mace® lachrymator, included various types of liquid based CN chemical formulae in pressurized aerosol spray containers. However, the lachrymator agents used in such sprays contain highly toxic and/or cancer causing chemicals. Furthermore, such technology used environmentally unfriendly carrier agent/solvents such as trichlorotrifluoroethanes (CFC's 111, 113) and cosmetic kerosene.

In an effort to overcome these problems, a pepper based inflammatory spray technology was developed and first introduced through the CAP-STUN® brand pepper spray in 1982 introduced into the self-protection market. Pepper sprays are available with various concentration of capsaicin (capsaicinoids), which is the primary ingredient producing the effects of pepper spray. Various types of pepper sprays have since come into existence; however, the technology of pepper spray is still basically unchanged since its inception.

Even though pepper sprays and other lachrymators are generally effective for self-defense purposes, improvements are still desired, particularly in decreasing the time for incapacitation while avoiding long term effects on the target. Law enforcement officials would like to be able to incapacitate a suspect for a sufficient time to allow immobilization while decreasing time spent under the influence of the pepper spray active ingredient. Excessive exposure to capsaicin may result in permanent harm or injury to the recipient, particularly damage to the eyes, skin, or upper respiratory tract. This has left unmet the need for an effective, shorter duration spray that can be used without long-term harm to the recipient, while reducing or eliminating any impact on the user and any bystanders, and reducing any adverse effects on the environment.

Other problems arise with defense spray applications, such as in pepper sprays and mace, where the spray is directed to the facial area. Here the solvent formulation requirements are stricter since they are intentionally sprayed on an individuals face, with exposure to eyes, skin and the respiratory system. Therefore, the solvent formulation should also pass toxicological tests showing no damage to the eyes, skin or upper respiratory tract. Furthermore, the solvent formulation must be miscible with the active ingredients in the defense spray.

The mechanism of action of capsaicin is known. It stimulates a nerve pathway, that of C-fiber sensory neurons, involved in the perception of pain. Although pepper sprays are effective, they currently have two defects. First, the duration of pain that they cause is excessively long, causing suffering. Second, they have been reported to be life threatening for a subpopulation of people, who suffer from asthma and have hypersensitive airways, although the magnitude of this concern is questioned. The current invention provides a composition, methods of use that overcome the above deficiencies, together with a manufacture incorporating such compositions.

SUMMARY OF THE INVENTION

In one aspect, the invention provides a composition comprising an effective amount of an agonist and an effective amount of an antagonist, wherein the amount of antagonist does not decrease a maximal response to agonist by more than 20%, compared to agonist alone, at time 0, and the amount of antagonist reduces the response to agonist by at least 80% at 20 minutes.

In another aspect, the invention provides a biocontrol agent comprising the composition as delineated above.

In certain aspects, the invention provides a method for incapacitating a subject, comprising: (a) providing a non-lethal temporarily incapacitating composition suitable for use in an aerosol or spray application, the incapacitating formulation comprising, an effective amount of a TRPV1 agonist, an effective amount of a TRPV1 antagonist, and a solvent system; and (b) applying the non-lethal temporarily incapacitating formulation to the subject; wherein the amount of antagonist does not decrease a maximal response to agonist by more than 20%, compared to agonist alone, at time 0, and the amount of antagonist reduces the response to agonist by at least 80% at 20 minutes.

In another aspect, the invention provides a method for subduing a subject, comprising: (a) providing a non-lethal temporarily incapacitating composition suitable for use in an aerosol or spray application, the incapacitating formulation comprising, an effective amount of an opiate agonist, an effective amount of an opiate antagonist, and a solvent system; and (b) applying the non-lethal temporarily incapacitating formulation to the subject; wherein the amount of antagonist does not decrease a maximal response to agonist by more than 20%, compared to agonist alone, at time 0, and the amount of antagonist reduces the response to agonist by at least 80% at 20 minutes.

DESCRIPTION OF THE DRAWINGS

FIG. 2A shows the calcium imaging curves for the combination of capsaicin and varying concentrations of the antagonist BCTC. FIG. 2B shows the calcium imaging curves for the combination of capsaicin and varying concentrations of the antagonist I-RTX. FIG. 2C shows the calcium imaging curves for the combination of capsaicin and varying concentrations of the antagonist JYL-827. FIG. 2D shows the calcium imaging curves for the combination of capsaicin and varying concentrations of the antagonist AMG9810. FIG. 2E shows the calcium imaging curves for the combination of capsaicin and varying concentrations of the antagonist capsazepine. Note for FIG. 2D and especially FIG. 2E the decrease in the initial response to capsaicin as the ratio of antagonist to agonist is raised.

FIGS. 3A, 3B, 3C, 3D, and 3E show the level of calcium induced by capsaicin and the decreased level of calcium induced in the presence of different ratios of antagonist to agonist at three times, those of maximal stimulation, of 200 sec after ligand addition, and of 600 sec after ligand addition. The dashed lines represent the levels of inhibition corresponding to 20% inhibition of the response to capsaicin alone and to 80% inhibition of maximal response. Data is presented for three different amounts of agonist. FIG. 3A includes the combination of capsaicin and BCTC; FIG. 3B includes the combination of capsaicin and I-RTX; FIG. 3C includes the combination of capsaicin and JYL-827; FIG. 3D includes the combination of capsaicin and AMG9810; FIG. 3E includes the combination of capsaicin and capsazepine.

DETAILED DESCRIPTION OF THE INVENTION

Compositions of the Invention

Figure 1:
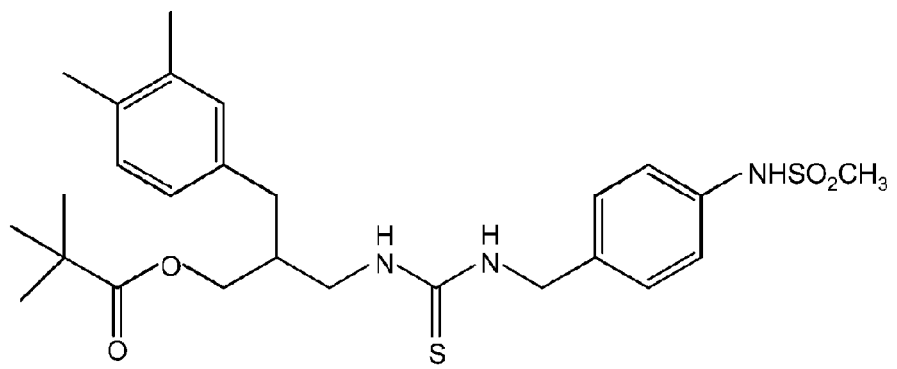
FIG. 1 provides the structures and names of a TRPV1 agonist (capsaicin), as well as the structures and names of various TRPV1 antagonists.
Figure 1:
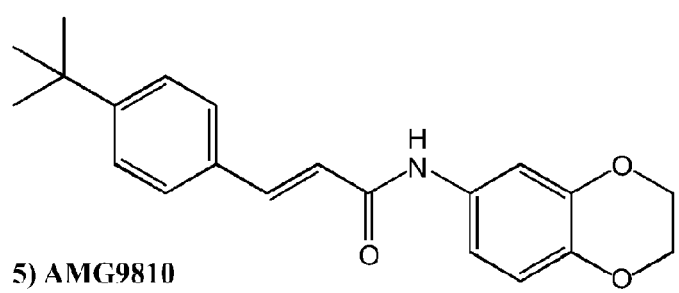
Figure 1:
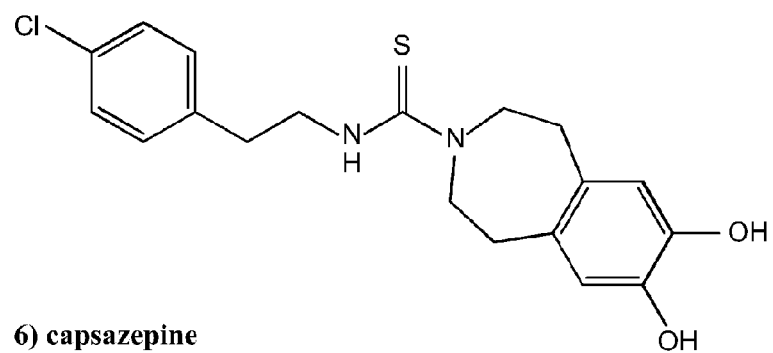
Figure 2A:
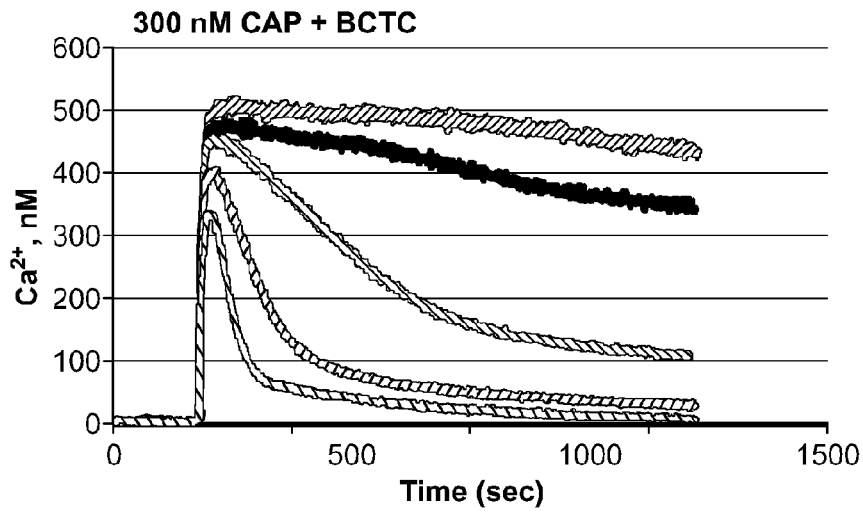
FIGS. 2A, 2B, 2C, 2D, and 2E illustrate the persistent elevation of intracellular calcium in CHO cells expressing TRPV1 and the progressively enhanced suppression of the capsaicin response with time when cells were treated with the combination of agonist plus antagonist at increasing ratios.
Figure 2B:
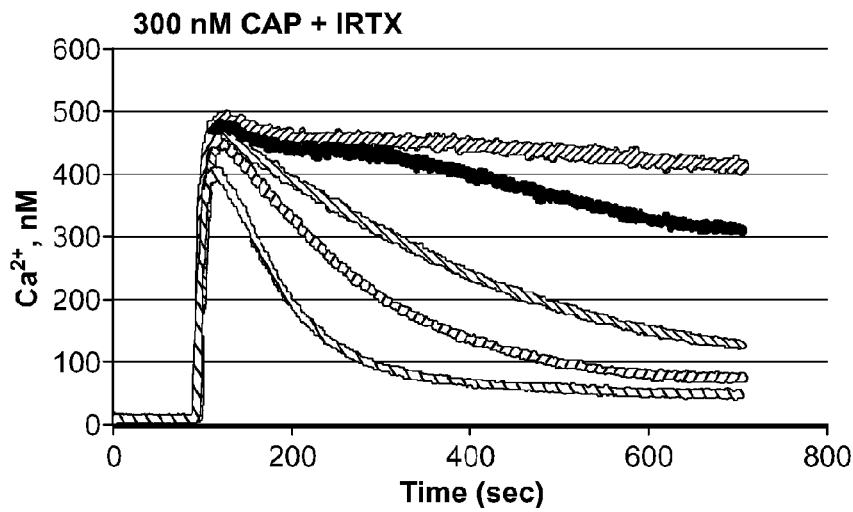
Figure 2C:
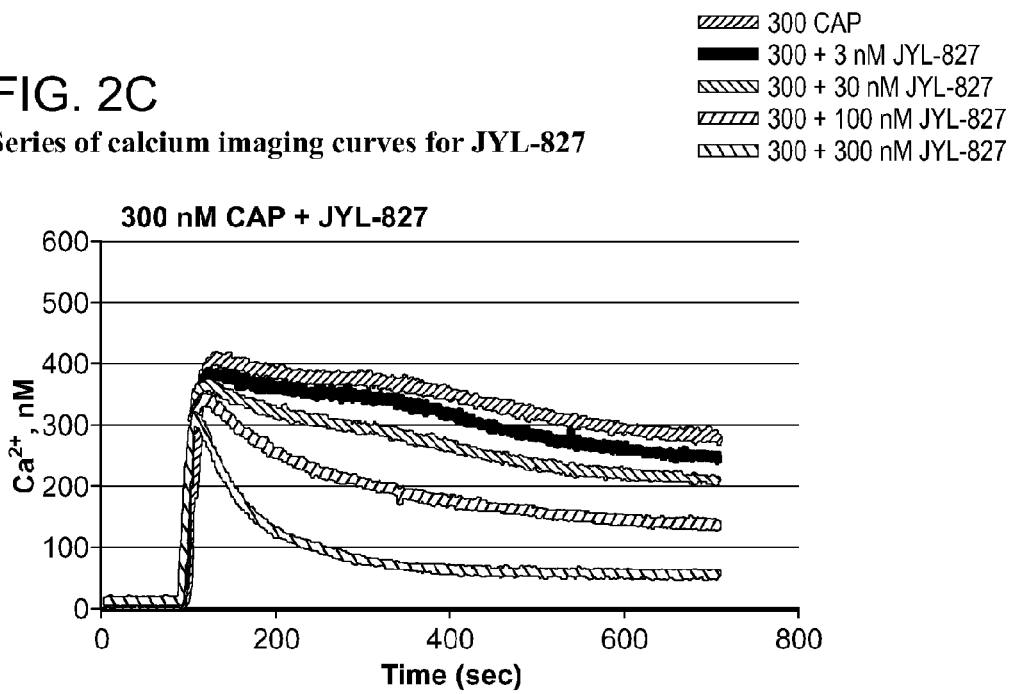
Figure 2D:
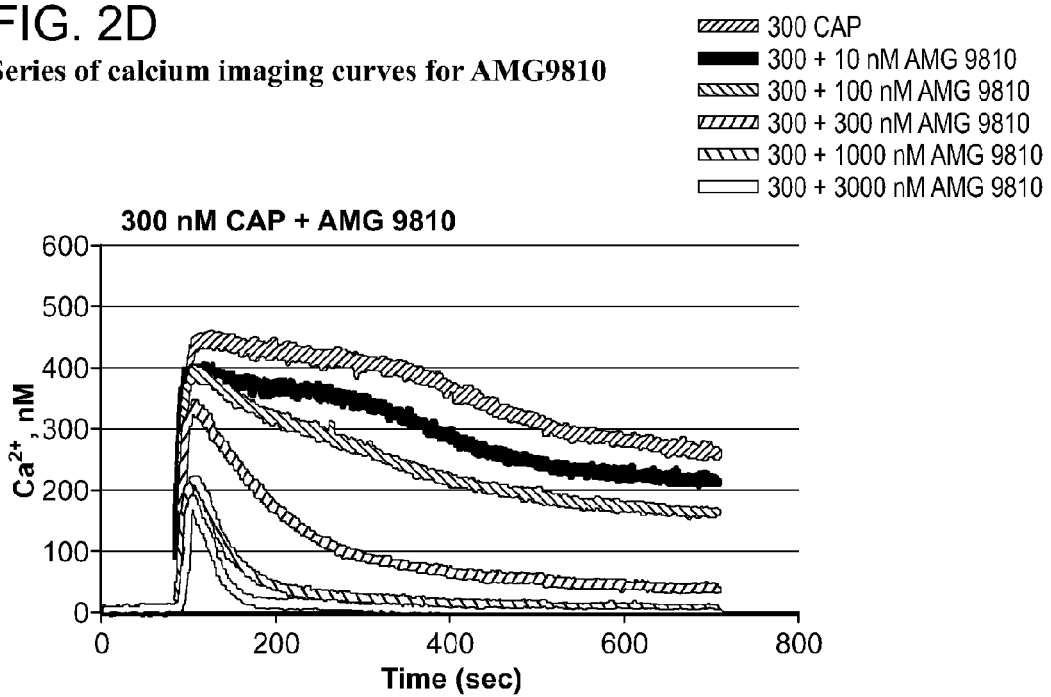
Figure 2E:
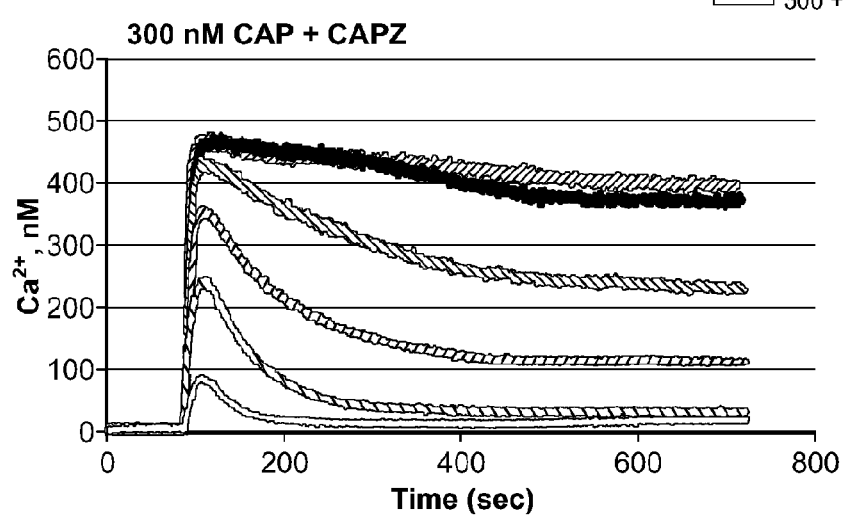
Figure 3A:
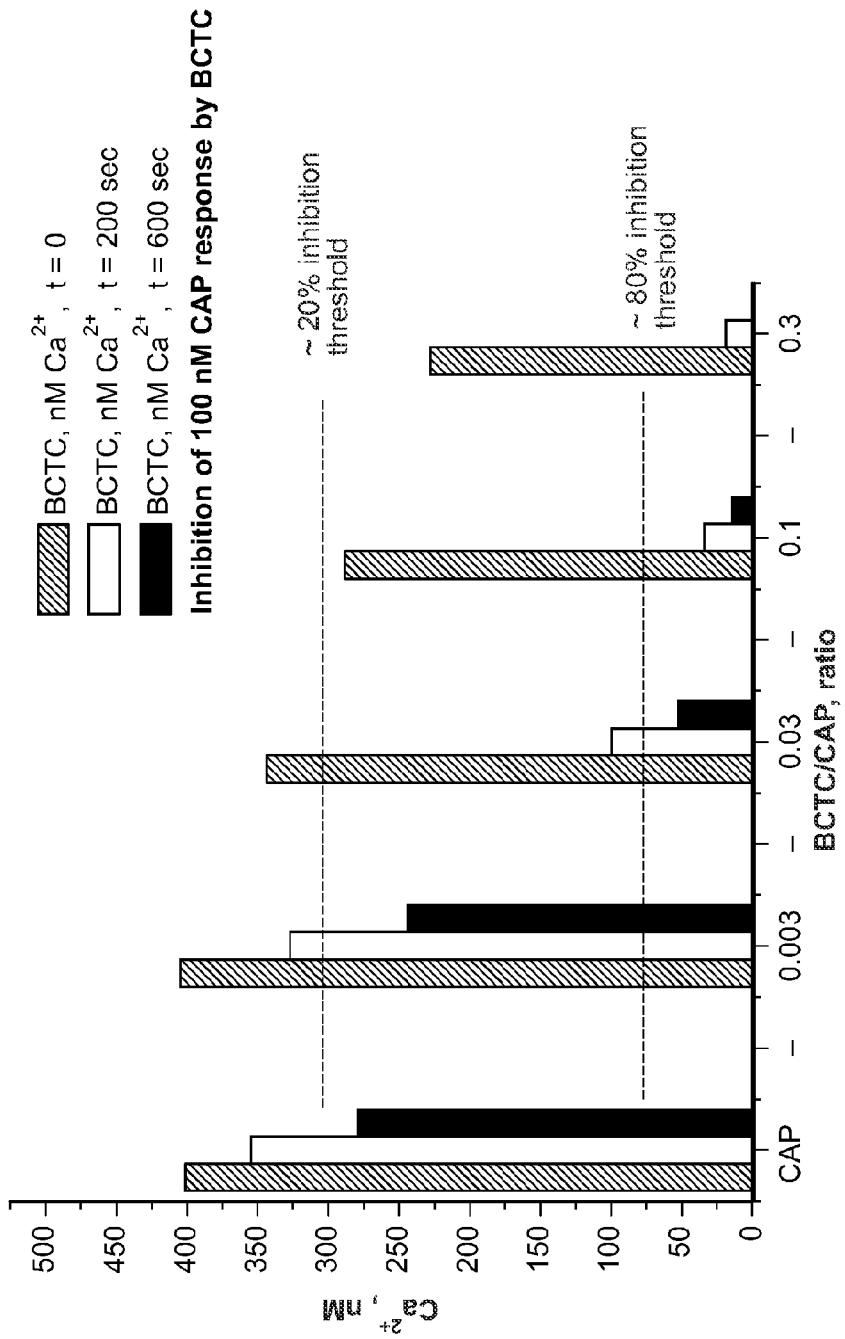
Figure 3A:
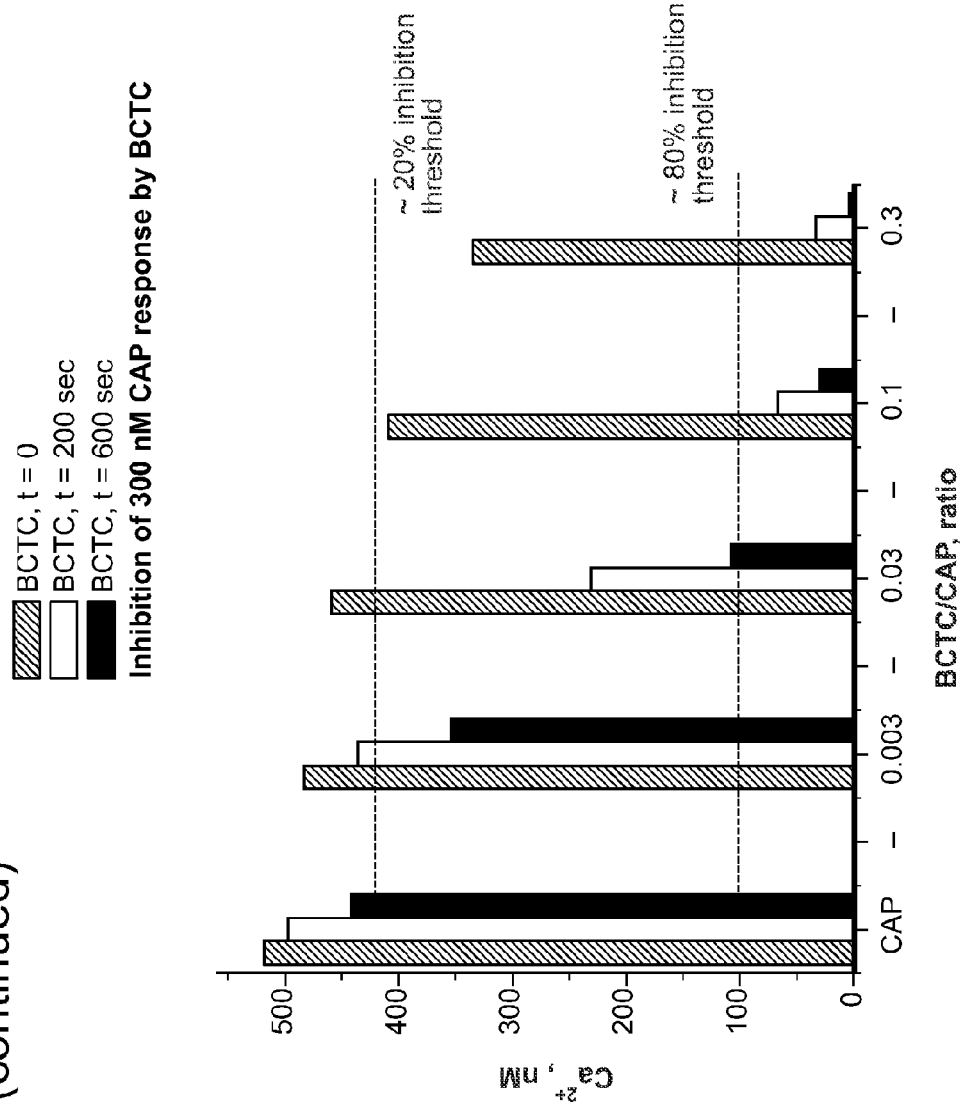
Figure 3A:
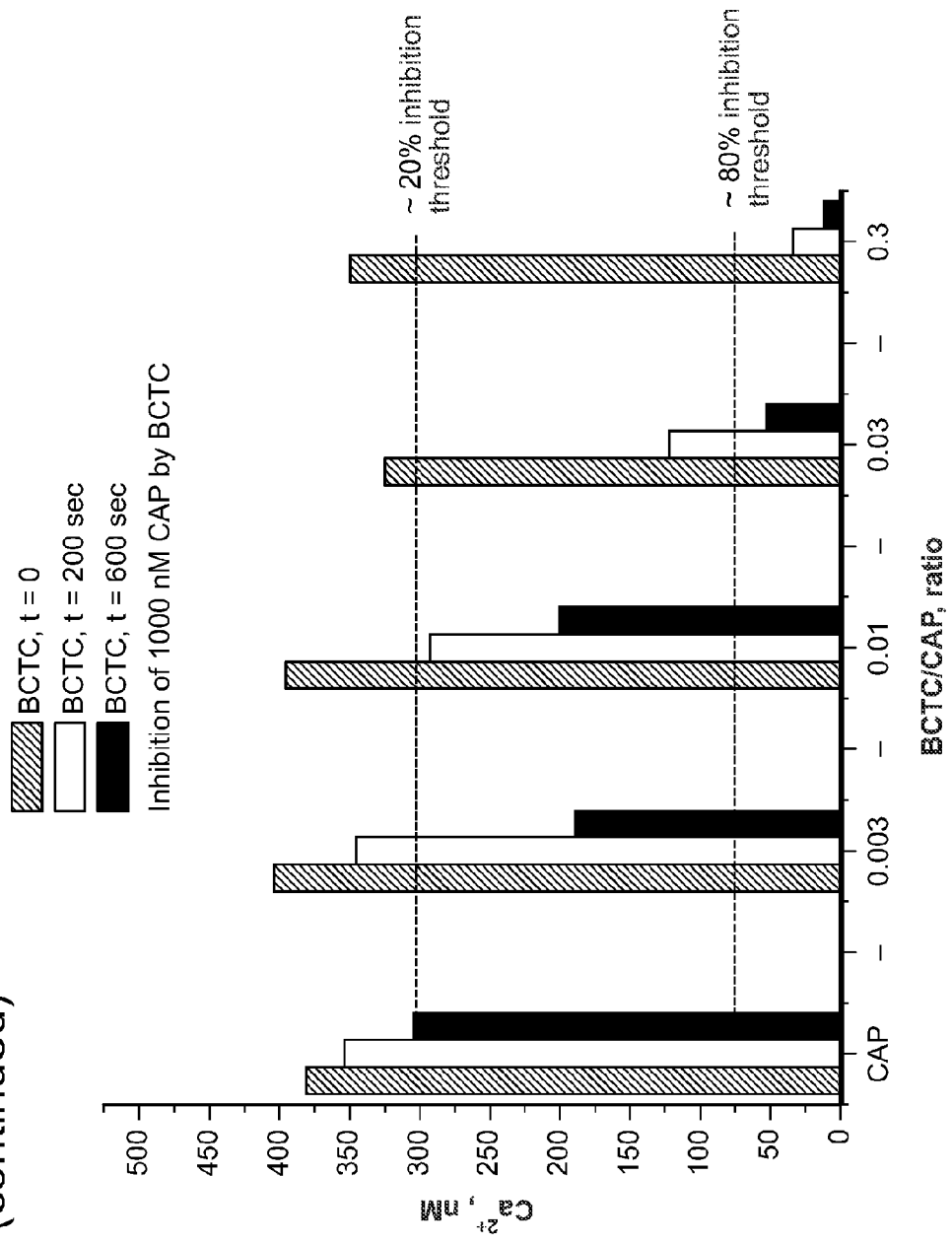
Figure 3B:
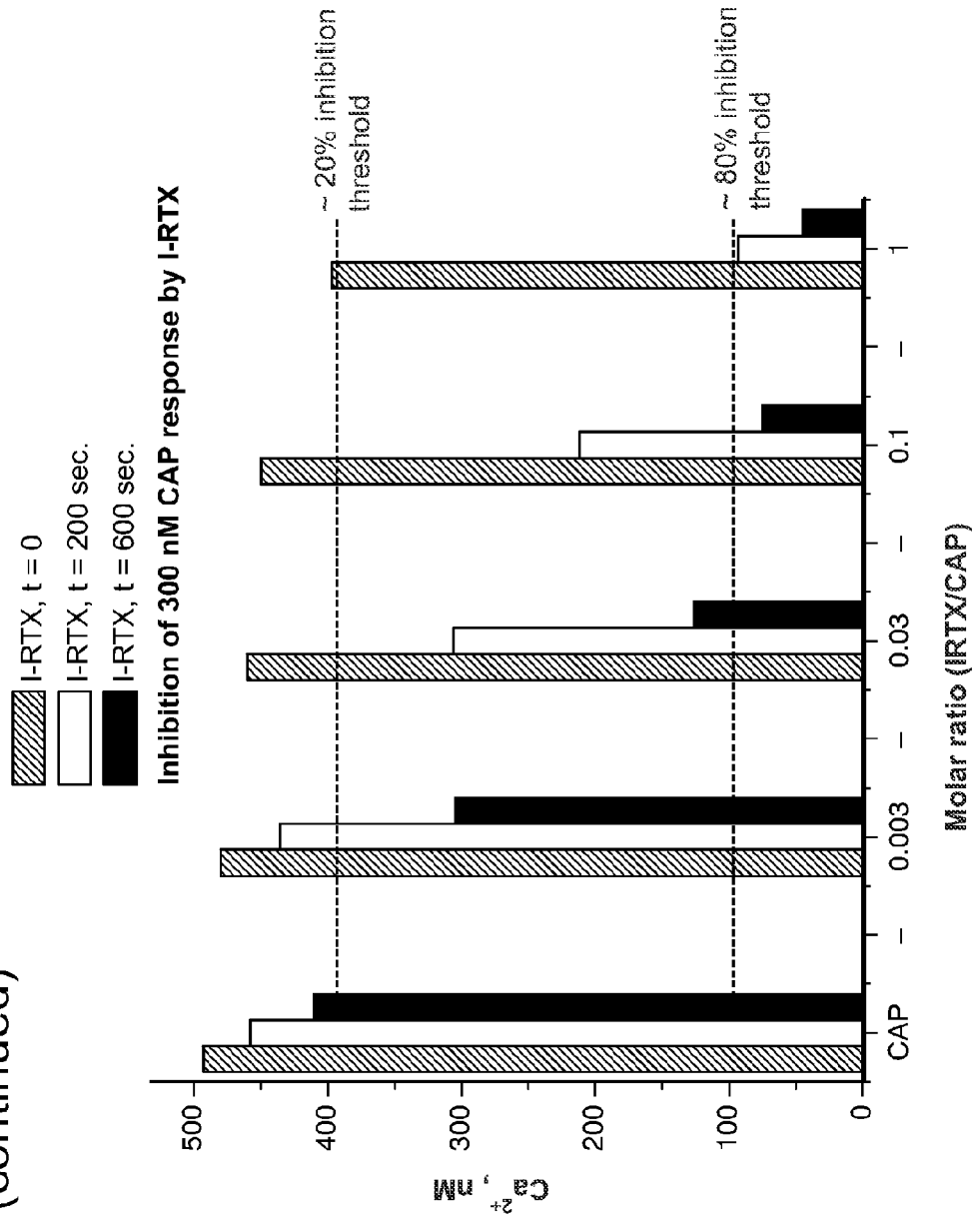
Figure 3B:
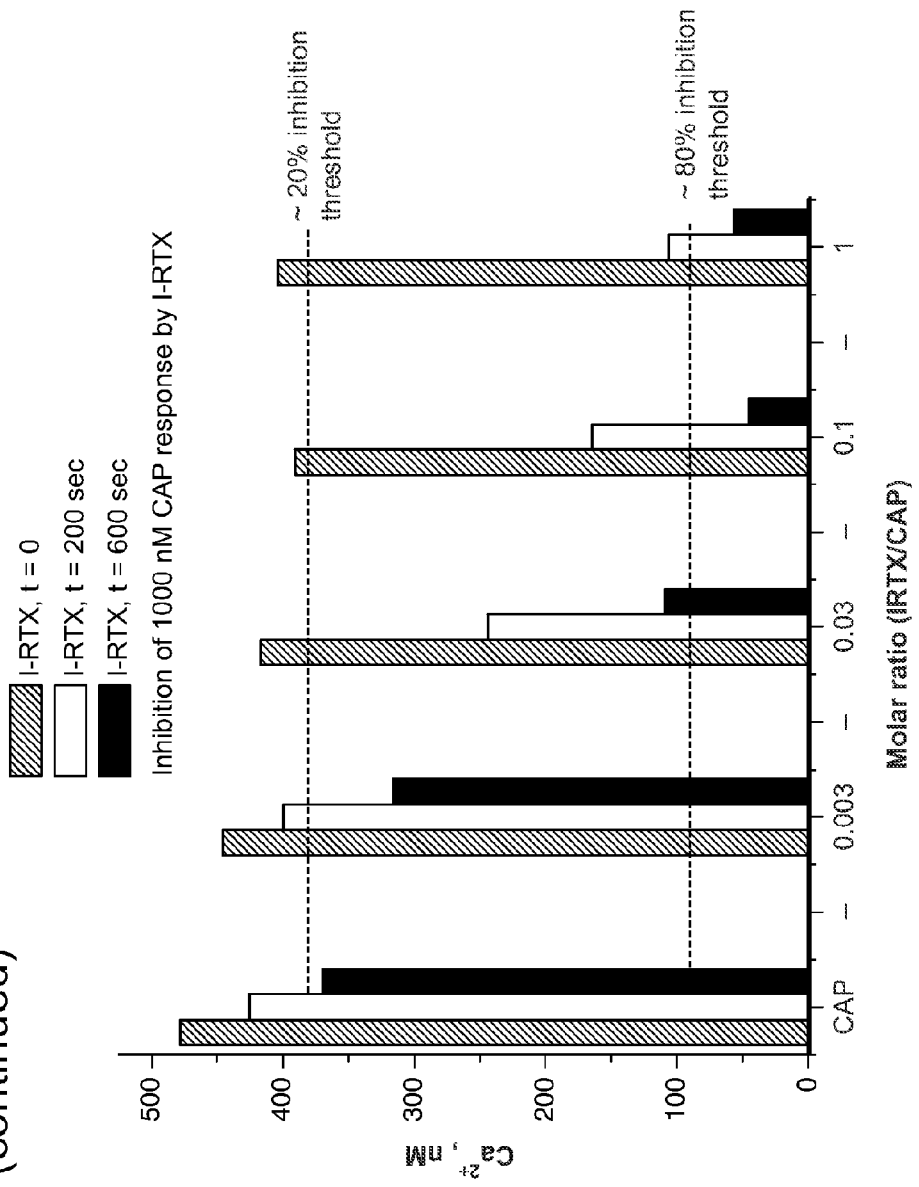
Figure 3C:
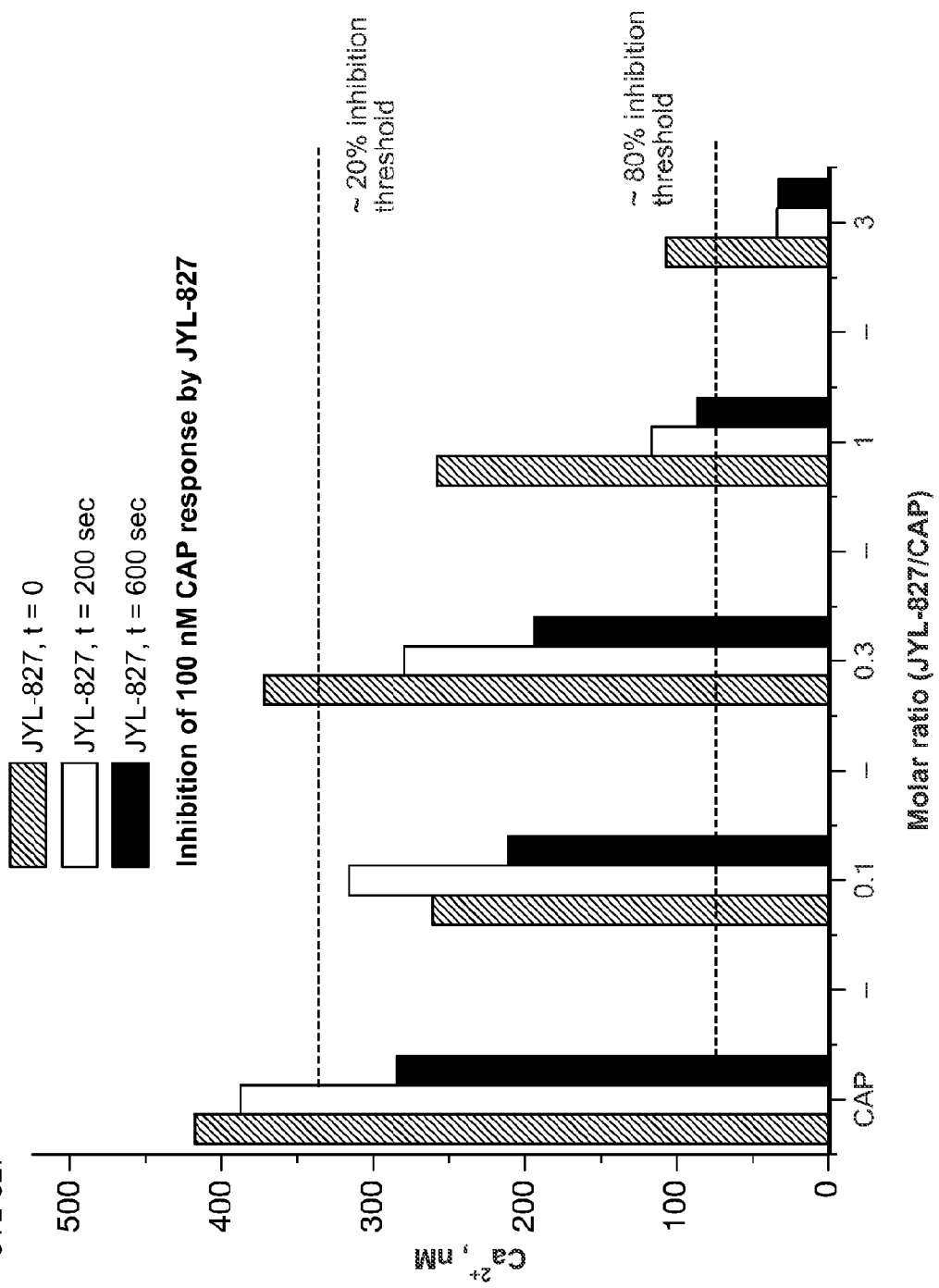
Figure 3C:
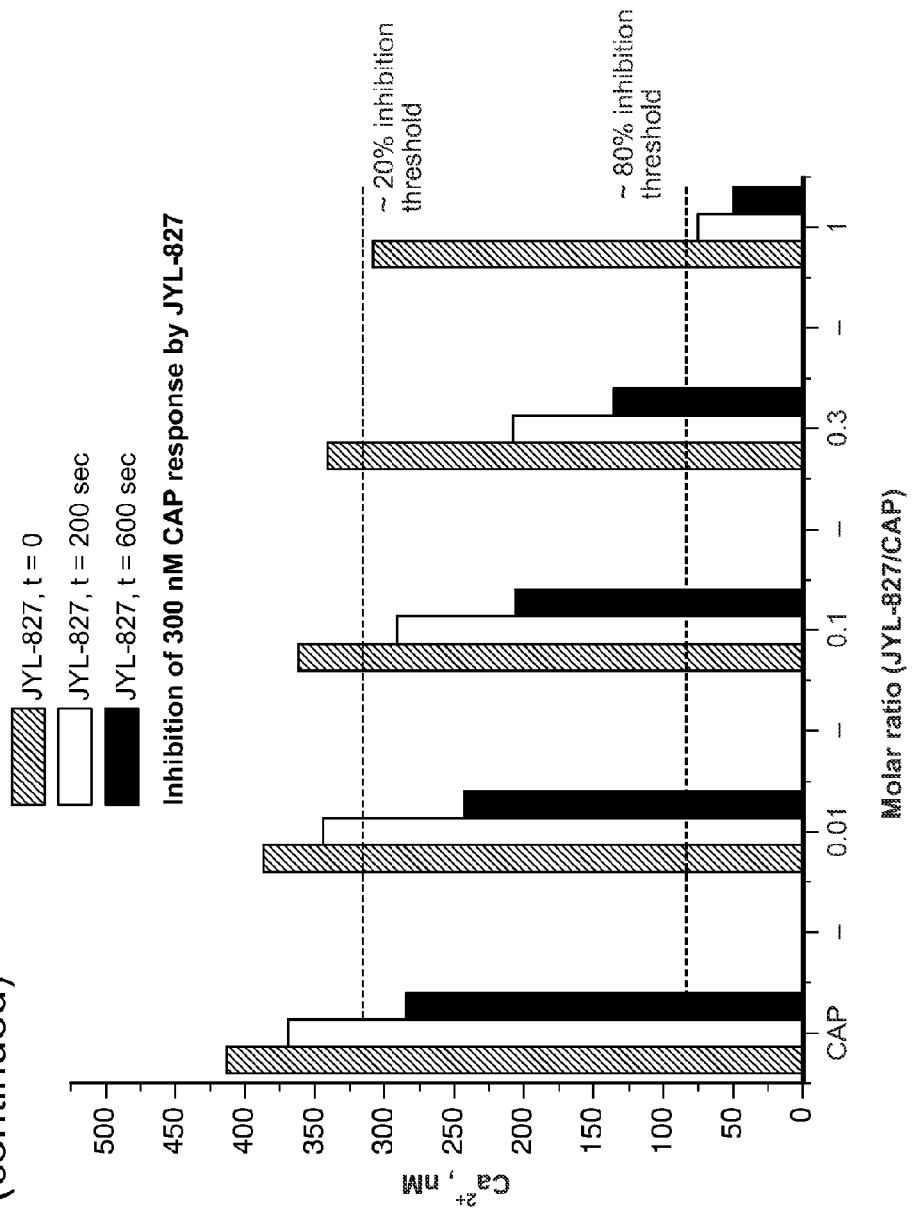
Figure 3C:
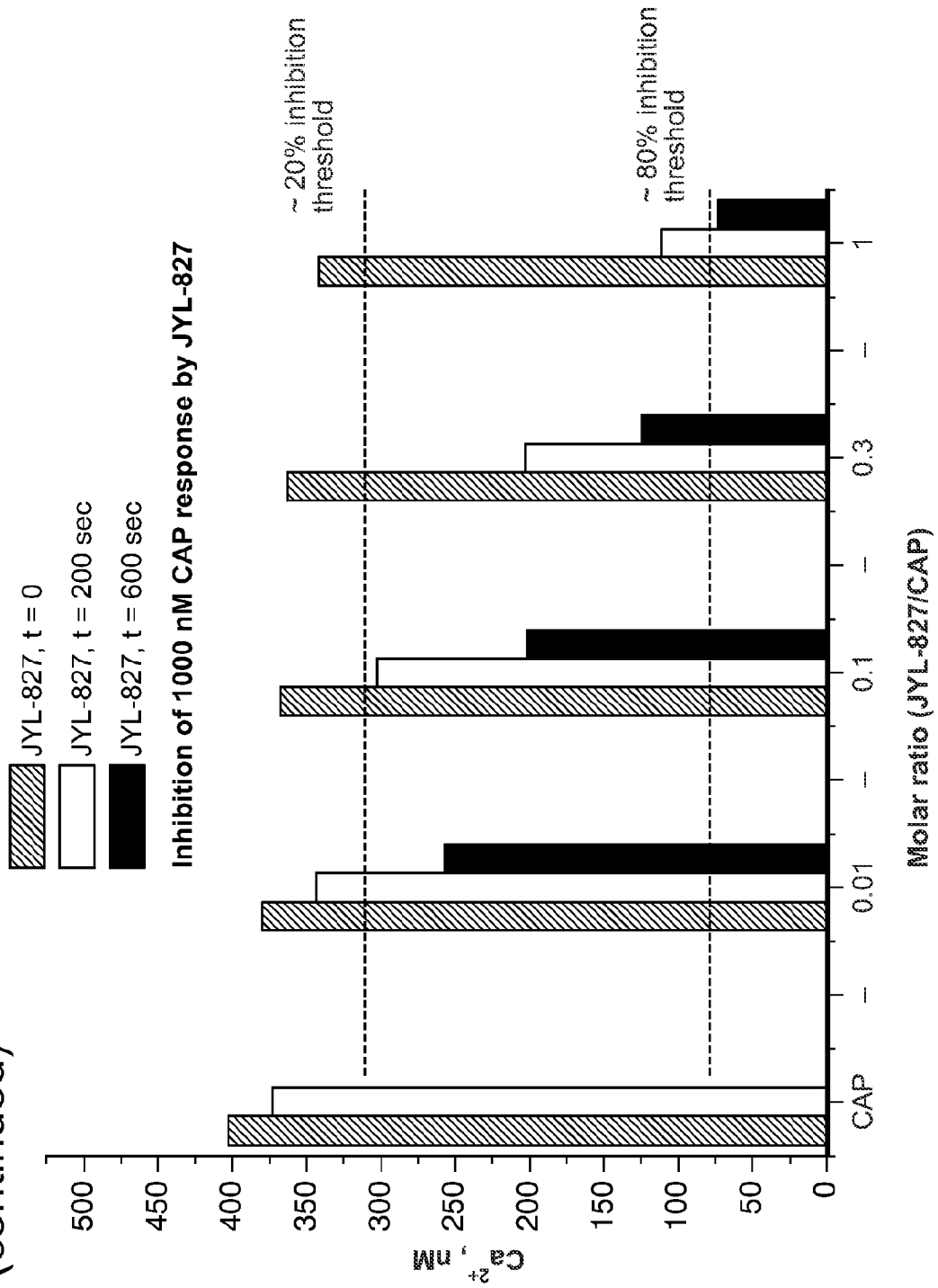
Figure 3D:
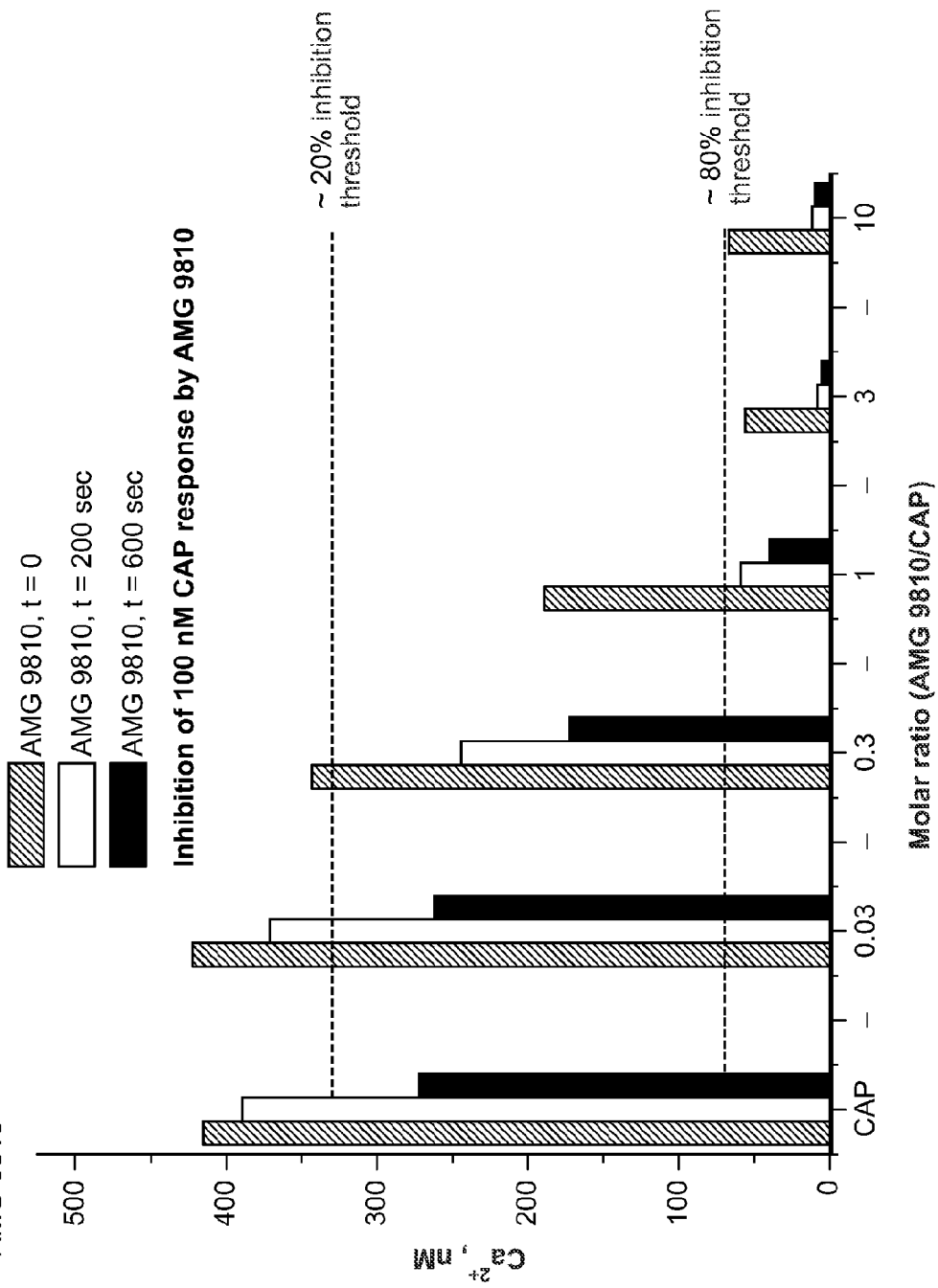
Figure 3D:
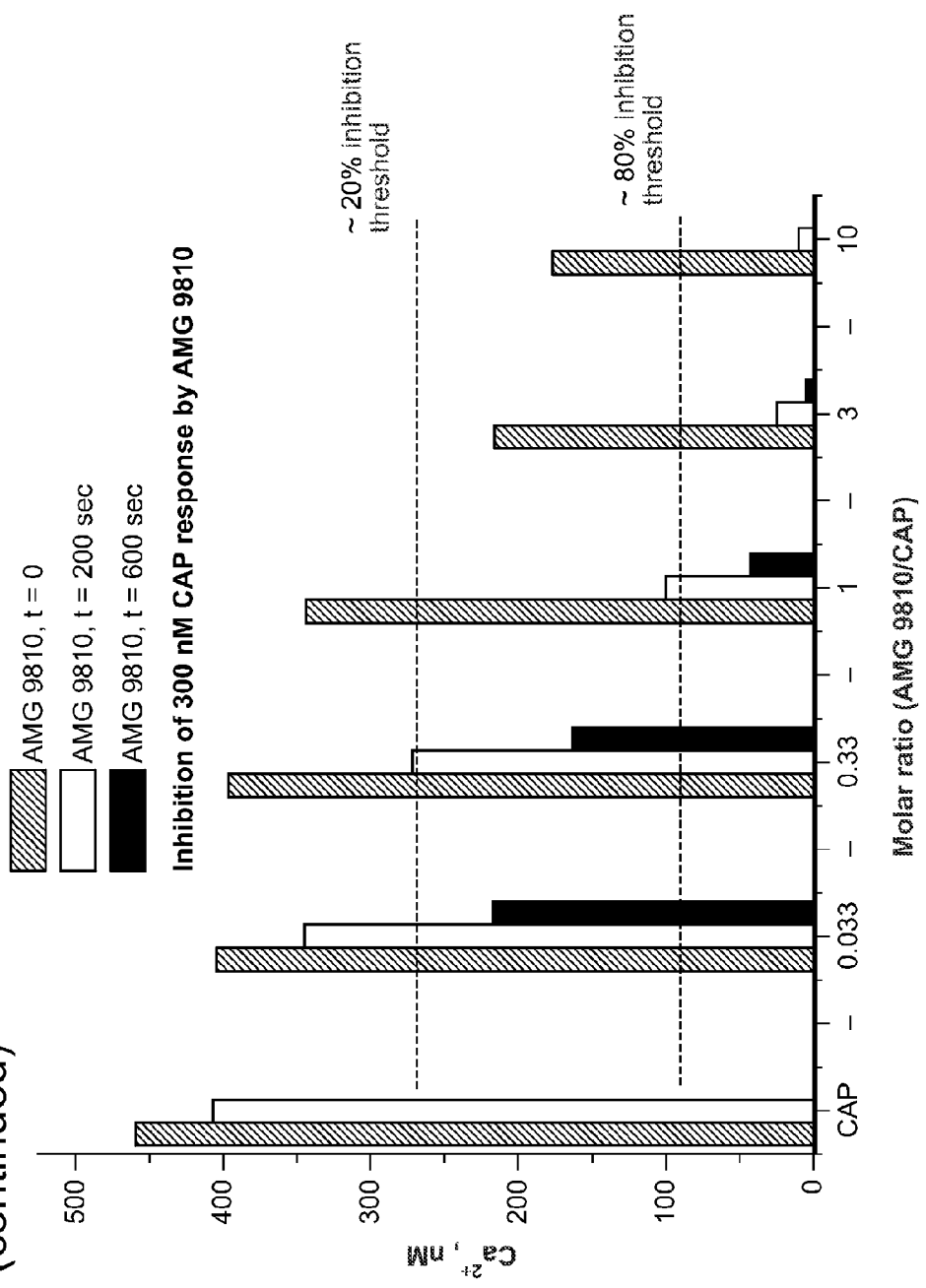
Figure 3D:
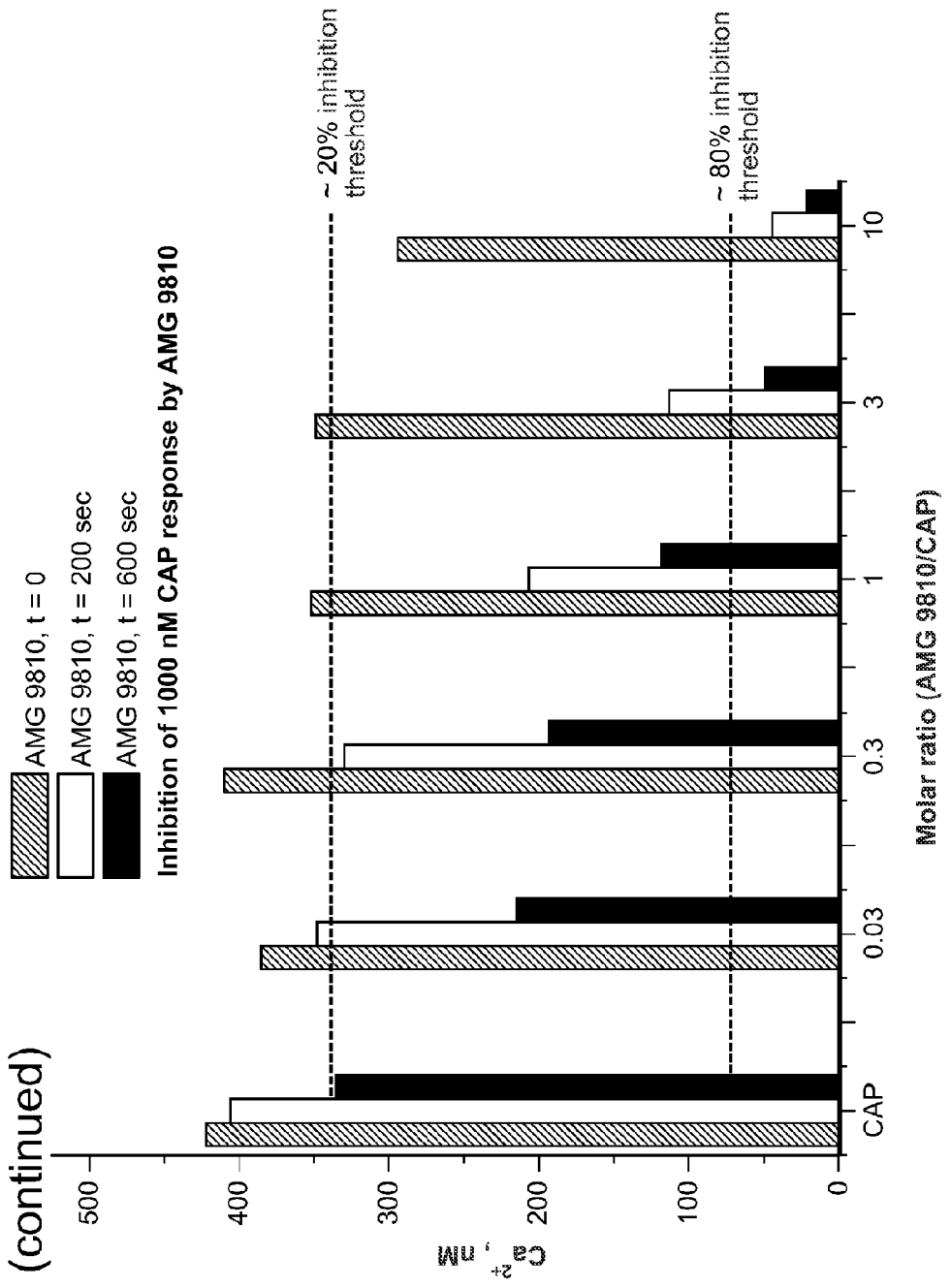

In one aspect, the invention provides a composition comprising an effective amount of an agonist and an effective amount of an antagonist, wherein the amount of antagonist does not decrease a maximal response to agonist by more than 20%, compared to agonist alone, at time 0, and the amount of antagonist reduces the response to agonist by at least 80% at 20 minutes.

In a first embodiment, the agonist is a TRPV1 agonist and the antagonist is a TRPV1 antagonist, wherein the TRPV1 agonist has a rate of penetration that is faster than the TRPV1 antagonist.

In certain embodiments, the TRPV1 agonist is antagonized by 80% by the TRPV1 antagonist, in about 1 minute to about 20 minutes. In a further embodiment, the TRPV1 agonist is antagonized by 80% by the TRPV1 antagonist, in about 1 minute to about 5 minutes.

In other embodiments, the TRPV1 agonist is capsaicin, dibenzoxazepine (CR), oleoresin capscium (OC), oleoresin paprika, paprika, capsicums (chili peppers), trans-8-methyl-N-vanillyl-6-nonenamide (capsaicin), 8-methyl-N-vanillyl-nonamide (dihydrocapsaicin), 7-methyl-N-vanillyl-octamide (nordihydrocapsaicin), 9-methyl-N-vanillyl-decamide (homodihydrocapsaicin), trans-9-methyl-N-vanillyl-7-decenamide (homocapsaicin), (3R,3,5R)-3,3'-dihydroxy-a,k-caroten-6'-one (capsanthin), N-vanillyl-octamide, N-vanillyl-nonamide, N-vanillyl-decanamide, N-vanillyl-undecanamide, N-vanillyl-paaiperic acid amide, nonivamide, civamide, olvanil, Nb-VNA, Nv-VNA, SB-705498, or anadamide. In a further embodiment, the TRPV1 agonist is capsaicin.

In other embodiments, the TRPV1 antagonist is BCTC, IodoRTX, JYL-827, AMG9810, capsazepine, SB-705498, Aprepitant, Lanpepitant, CP-99,994, SDZ NKT 343, Ezlopitant, CP-96345, CP-99994, CP-122721, MK-869, GR 205171. RP 67580, Dapitant, Lanepitant, Noloitanium, Sarefutant, Casopitant, or Vestipitant. In a further embodiment, the TRPV1 antagonist is BCTC, IodoRTX, JYL-827, AMG9810, or capsazepine.

In a second embodiment, the invention provides a composition wherein the agonist is an opiate agonist and the antagonist is an opiate antagonist.

In certain embodiments, the opiate agonist is fentanyl.

In other embodiments, the opiate antagonist is diphenyl-6beta-naltrexamate or 6-beta-tosylnaltrexamate.

In certain embodiments, the agonist and antagonist are in a ratio of about 1:1 to about 10:1.

In various embodiments, the agonist and antagonist are in a ratio of about 1:1 to about 1:10.

In other embodiments, the invention provides a composition further comprising an additional therapeutic agent.

In another embodiment, the invention provides a composition further comprising a surfactant, solubilizer, or emulsifier.

In another aspect, the invention provides a biocontrol agent comprising the composition as delineated above.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt form, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of the Invention

In certain aspects, the invention provides a method for incapacitating a subject, comprising:
(a) providing a non-lethal temporarily incapacitating composition suitable for use in an aerosol or spray application, the incapacitating formulation comprising,
an effective amount of a TRPV1 agonist, an effective amount of a TRPV1 antagonist, and a solvent system; and
(b) applying the non-lethal temporarily incapacitating formulation to the subject;
wherein the amount of antagonist does not decrease a maximal response to agonist by more than 20%, compared to agonist alone, at time 0, and the amount of antagonist reduces the response to agonist by at least 80% at 20 minutes.

In one embodiment, the invention provides a method wherein the non-lethal temporarily incapacitating composition further comprises a propellant. In a further embodiment, the propellant is miscible in said solvent system. In a further embodiment, the propellant is carbon dioxide.

In other embodiments, the invention provides a method wherein the TRPV1 agonist is antagonized by 80% by the TRPV1 antagonist, in about 1 minute to about 20 minutes. In a further embodiment, the TRPV1 agonist is antagonized by 80% by the TRPV1 antagonist, in about 1 minute to about 5 minutes.

In certain embodiments, the invention provides a method wherein the TRPV1 agonist is capsaicin, dibenzoxazepine (CR), oleoresin capscium (OC), oleoresin paprika, paprika, capsicums (chili peppers), trans-8-methyl-N-vanillyl-6-nonenamide (capsaicin), 8-methyl-N-vanillyl-nonamide (dihydrocapsaicin), 7-methyl-N-vanillyl-octamide (nordihydrocapsaicin), 9-methyl-N-vanillyl-decamide (homodihydrocapsaicin), trans-9-methyl-N-vanillyl-7-decenamide (homocapsaicin), (3R,3,5R)-3,3'-dihydroxy-a,k-caroten-6'-one (capsanthin), N-vanillyl-octamide, N-vanillyl-nonamide, N-vanillyl-decanamide, N-vanillyl-undecanamide, N-vanillyl-paaiperic acid amide, nonivamide, civamide, olvanil, Nb-VNA, Nv-VNA, SB-705498, or anadamide. In a further embodiment, the TRPV1 agonist is capsaicin.

In certain embodiments, the invention provides a method wherein the TRPV1 antagonist is BCTC, IodoRTX, JYL-827, AMG9810, or capsazepine, SB-705498, Aprepitant, Lanpepitant, CP-99,994, SDZ NKT 343, Ezlopitant, CP-96345, CP-99994, CP-122721, MK-869, GR 205171. RP 67580, Dapitant, Lanepitant, Noloitanium, Sarefutant, Casopitant, or Vestipitant. In a further embodiment, the TRPV1 antagonist is BCTC, IodoRTX, JYL-827, AMG9810, or capsazepine.

In certain embodiments, the invention provides a method wherein the TRPV1 agonist and antagonist are present in an amount of about 0.01% to about 5% by weight of the solvent system. In a further embodiment, the TRPV1 agonist and antagonist are present in an amount of 0.1% to about 3% by weight of the solvent system.

In other embodiments, the invention provides a method wherein the solvent system comprises approximately equal amounts of the propylene glycol dicaprylate/caprate and glycerol tris(2-ethylhexanoate).

In certain embodiments, the invention provides a method wherein said applying comprises spraying the non-lethal temporarily incapacitating formulation into the eyes of the subject.

In still other embodiments, the invention provides a method wherein said incapacitating composition is formulated to cause, upon application of the system to the facial area of a recipient, inflammation to the facial area of the recipient.

In other embodiments, the invention provides a method wherein said application of the composition into the facial area of the subject causes the subject to experience a symptom selected from the group consisting of immediate closing of the eyes, shortness of breadth, and burning sensation.

In a further embodiment, the symptom lasts about 1 minute to about 45 minutes.

In another aspect, the invention provides a method for subduing a subject, comprising:
(a) providing a non-lethal temporarily incapacitating composition suitable for use in an aerosol or spray application, the incapacitating formulation comprising, an effective amount of an opiate agonist, an effective amount of an opiate antagonist, and a solvent system; and (b) applying the non-lethal temporarily incapacitating formulation to the subject; wherein the amount of antagonist does not decrease a maximal response to agonist by more than 20%, compared to agonist alone, at time 0, and the amount of antagonist reduces the response to agonist by at least 80% at 20 minutes.

In one embodiment, the invention provides a method wherein the non-lethal temporarily incapacitating composition further comprises a propellant. In a further embodiment, the propellant is miscible in said solvent system. In a further embodiment, the propellant is carbon dioxide.

In other embodiments, the invention provides a method wherein the TRPV1 agonist is antagonized by 80% by the TRPV1 antagonist, in about 1 minute to about 20 minutes. In a further embodiment, the TRPV1 agonist is antagonized by 80% by the TRPV1 antagonist, in about 1 minute to about 5 minutes.

In certain embodiments, the invention provides a method wherein the TRPV1 agonist is capsaicin, dibenzoxazepine (CR), oleoresin capscium (OC), oleoresin paprika, paprika, capsicums (chili peppers), trans-8-methyl-N-vanillyl-6-nonenamide (capsaicin), 8-methyl-N-vanillyl-nonamide (dihydrocapsaicin), 7-methyl-N-vanillyl-octamide (nordihydrocapsaicin), 9-methyl-N-vanillyl-decamide (homodihydrocapsaicin), trans-9-methyl-N-vanillyl-7-decenamide (homocapsaicin), (3R,3,5R)-3,3'-dihydroxy-a,k-caroten-6'-one (capsanthin), N-vanillyl-octamide, N-vanillyl-nonamide, N-vanillyl-decanamide, N-vanillyl-undecanamide, N-vanillyl-paaiperic acid amide, nonivamide, civamide, olvanil, Nb-VNA, Nv-VNA, SB-705498, or anadamide. In a further embodiment, the TRPV1 agonist is capsaicin.

In certain embodiments, the invention provides a method wherein the TRPV1 antagonist is BCTC, IodoRTX, JYL-827, AMG9810, or capsazepine, SB-705498, Aprepitant, Lanpepitant, CP-99,994, SDZ NKT 343, Ezlopitant, CP-96345, CP-99994, CP-122721, MK-869, GR 205171. RP 67580, Dapitant, Lanepitant, Noloitanium, Sarefutant, Casopitant, or Vestipitant. In a further embodiment, the TRPV1 antagonist is BCTC, IodoRTX, JYL-827, AMG9810, or capsazepine.

In certain embodiments, the invention provides a method wherein the TRPV1 agonist and antagonist are present in an amount of about 0.01% to about 5% by weight of the solvent system. In a further embodiment, the TRPV1 agonist and antagonist are present in an amount of 0.1% to about 3% by weight of the solvent system.

In other embodiments, the invention provides a method wherein the solvent system comprises approximately equal amounts of the propylene glycol dicaprylate/caprate and glycerol tris(2-ethylhexanoate).

In certain embodiments, the invention provides a method wherein said applying comprises spraying the non-lethal temporarily incapacitating formulation into the eyes of the subject.

In still other embodiments, the invention provides a method wherein said incapacitating composition is formulated to cause, upon application of the system to the facial area of a recipient, inflammation to the facial area of the recipient.

In other embodiments, the invention provides a method wherein said application of the composition into the facial area of the subject causes the subject to experience a symptom selected from the group consisting of immediate closing of the eyes, shortness of breadth, and burning sensation.

In a further embodiment, the symptom lasts about 1 minute to about 45 minutes.

It has now been discovered that the non-lethal formulation of the present invention, using the novel agonist and antagonist system, provides a shorter lasting incapacitation period, and does so without lasting or toxic effects on the recipient. The compositions of the invention are selected so that the agonist is a fast penetrating agonist, while the antagonist is a slower penetrating antagonist, allowing for agonist action followed by antagonist action. In certain embodiments, the agonist is a TRPV1 agonist and the antagonist is a TRPV1 antagonist.

In one aspect, the invention provides composition comprising an agonist and an antagonist, in which the choice of agonist and antagonist is restricted so that the agonist is rapidly penetrating and the antagonist is slowly penetrating into cells and further where the proportions of agonist and antagonist are such that the rapidly penetrating agonist can first exert its agonist effect and then, as the antagonist penetrates, the antagonist is able to antagonize the further action of the agonist.

In another aspect, the invention provides a method of use, in which the duration of activity of an agonist can be limited, independent of the administered dose of the agonist over a broad range, by simultaneously administering a fixed ratio of agonist and antagonist, in which the agonist utilized has the characteristic of being absorbed quickly and the antagonist utilized has the characteristic of being absorbed slowly. The desirable ratio of agonist and antagonist is such that the antagonist, upon uptake, is present in sufficient quantity to largely antagonize the agonist, and where the ratio of agonist to antagonist is further selected to give the desired duration of action of the agonist.

In certain aspects, the invention provides the use of an opiate agonist and an opiate antagonist for military or law enforcement purposes. In certain embodiments, the opiate agonist is fentanyl. In certain embodiments, the opiate antagonist is diphenyl-6-beta-altrexamate or 6-beta-tosylnaltrexamate. In such preparations, the opiate antagonists are absorbed at a rate that is slower than the opiate agonist. Such compositions are useful for subduing individuals in an assemblage of people, in which consequences of opiate agonist action are minimized for innocent bystanders.

The invention also provides a device, consisting of the above described mixture of agonist and antagonist, together with a spray device for projecting the mixture in the form of a spray, aerosol, or other dispersion.

One advantage of the invention is that the duration of an agonist when administered alone, is controlled by the dose administered, in which metabolism or redistribution limits the duration of the effect by reducing over time the concentration below its effective level. The current invention provides for a simultaneous administration of agonist and antagonist. An additional embodiment of the invention relates to the duration over which the agonist effect is desired, being seconds to minutes rather than hours or days.

The specific advantage of one embodiment of the current invention is that it provides an improved pepper spray with enhanced safety over current products. In certain aspects, the invention provides a mixture of an agonist together with an antagonist whereby, when administered to an individual in the form of a spray, a painful stimulation will be achieved and consequent incapacitation will occur for only a brief period compared to the current, state of the art capsaicin sprays.

One aspect of the invention consists of a device. The device comprises a means for spraying, together with said compositions of matter, where the compositions of matter comprise a mixture of an agonist for the capsaicin receptor TRPV1 together with an antagonist for TRPV1, whereby the agonist is selected from any known TRPV1 agonists such that it is rapidly penetrating into cells and the antagonist is selected from any known TRPV1 antagonists such that it is slowly penetrating into cells.

The proportions of agonist and antagonist under the invention are selected, based on the relative potencies of the agonist and the antagonist, the fast rate of penetration of the agonist, and the slow rate of penetration of the antagonist, such that the agonist will be antagonized by 80% between 1 and 20 min. In one embodiment, the agonist will be antagonist by 80% at 3.33 min.

Another aspect of the invention provides a method of use, whereby said compositions of matter are administered in spray, aerosol, or other fine dispersion to a subject person or animal so as to temporarily incapacitate said person or animal.

The unexpected and surprising advantage of the current invention is the combination of an antagonist of appropriate slow penetration together with a quickly acting agonist which gives a transient agonist response largely independent of the dose of agonist used. The general learning of those skilled in the art is that response to an agonist will follow the relationship response=response$_{max}$*(agonist concentration)/(agonist concentration+Kd for the agonist). Duration of response will be proportional to dose. Under conditions of administration of a repellent spray, the delivered dose is subject to wide variations and, in the case of capsaicin, is of long duration. The invention solves both of these problems.

Another advantage provided by the compositions of the invention is the identification of utility for the design of a combination of TRPV1 agonist and antagonist whose agonist action is of markedly limited duration independent of administered dose, viz. incorporation into a spray or aerosol or fine dispersion to achieve shorter lasting repellency largely independent of administered dose. This utility is significant, since minimizing pain to persons or animals subjected to such repellent spray is desirable in all cases and, by limiting duration of effect, may save the danger to persons or animals with hypersensitive airways. The invention thus addresses a health concern of a disadvantaged minority. The state of the art would hold that incorporation of an effective amount of an antagonist together with the agonist would render the mixture inactive and therefore without rationale for administration.

The following provides a way to determine the amounts of TRPV1 agonist and antagonist:

Let the measured potency of the agonist be: EC50agonist

Let the measured potency of the antagonist be: Klantagonist

Agonists used in this invention will be drawn from any of those agonists of TRPV1 such that, when added to aqueous medium, it achieves 90% of its maximal effect on cells expressing TRPV1 within 120 sec. Alternatively, the agonist achieves 90% equilibration with cells under such conditions, whether said cells express or do not express TRPV1. The standard assay used by those skilled in the art for characterizing TRPV1 agonists is a calcium uptake assay, measuring the increase in intracellular calcium in response to agonist addition in cells expressing TRPV1. These assays for measuring agonist potency also provide the information confirming the rapid effect of the agonist.

Antagonists used in this invention will be drawn from any of those antagonists of TRPV1 such that, when added to aqueous medium in the presence of agonist, at the ratio of antagonist used the antagonist does not decrease the maximal response to agonist by more than 20% compared to agonist alone and it reduces the response to agonist by at least 80% at 20 min.

The proportion of the antagonist to the agonist will be determined by the formula:

(Amount antagonist)/(Amount agonist)=
(Ki antagonist)/(EC50 agonist)×10×(alpha)

Where amounts are expressed in moles; potencies are expressed in molar units; Alpha is a factor which is determined by the rate of penetration of the antagonist relative to the agonist, such that the duration of action of the agonist decreases to 20% of maximum within 1 to 20 min.

FIG. 1 provides the structures and names of a TRPV1 agonist (capsaicin), as well as the structures and names of various TRPV1 antagonists.

FIGS. 2 and 3 provide two combinations of commercially available antagonists which can be combined with capsaicin to give the desired properties. These compounds are BCTC and Iodo-RTX. Additionally provided are the effects of three antagonists which were either marginal or failed to meet the criterion because ratios that gave a sufficient rate of decrease of the internal calcium level caused excessive loss of the initial capsaicin response.

It was observed that the effects were not fully independent of the dose of agonist because of the phenomenon of "spare receptors". Nonetheless, appropriate ratios of antagonist to agonist exist for BCTC and IodoRTX to achieve the response desired by the compositions of the invention.

FIGS. 2A-2E illustrate the persistent elevation of intracellular calcium in CHO cells expressing TRPV1 and the progressively enhanced suppression of the capsaicin response with time when cells were treated with the combination of agonist plus antagonist at increasing ratios. Note for FIG. 2D and especially FIG. 2E the decrease in the initial response to capsaicin as the ratio of antagonist to agonist is raised.

FIGS. 3A-3E show the level of calcium induced by capsaicin and the decreased level of calcium induced in the presence of different ratios of antagonist to agonist at three times, those of maximal stimulation, of 200 sec after ligand addition, and of 600 sec after ligand addition. The dashed lines represent the levels of inhibition corresponding to 20% inhibition of the response to capsaicin alone and to 80% inhibition of maximal response. Data is presented for three different amounts of agonist.

The term "subject" as used herein refers to a mammal. A subject therefore refers to, for example, dogs, cats, horses, cows, pigs, guinea pigs, and the like that are affected by the compounds used in the compositions of the invention. Preferably the subject is a human.

The term "time 0" refers to the time of administration.

Agonist and Antagonists

Any suitable agonist agent can be used in the composition of the present invention. In certain embodiments, the agonist is a TRPV1 agonist and include those of the inflammatory or irritant type and may be a pepper agent.

In certain embodiments, the incapacitating agent is a TRPV1 agonist including any known TRPV1 agonist including capsaicinoid compounds or capsaicin analogs, synthetic and natural oleoresin capsicum and capsaicins (including the entire family of capsaicinoids) capsaicin, dibenzoxazepine (CR), oleoresin capscium (OC), oleoresin paprika, paprika, capsicums (chili peppers), trans-8-methyl-N-vanillyl-6-nonenamide (capsaicin), 8-methyl-N-vanillyl-nonamide (dihydrocapsaicin), 7-methyl-N-vanillyl-octamide (nordihydrocapsaicin), 9-methyl-N-vanillyl-decamide (homodihydrocapsaicin), trans-9-methyl-N-vanillyl-7-decenamide (homocapsaicin), (3R,3,5R)-3,3'-dihydroxy-a,k-caroten-6'-one (capsanthin), N-vanillyl-octamide, N-vanillyl-nonamide, N-vanillyl-decanamide, N-vanillylundecanamide, N-vanillyl-paaiperic acid amide, nonivamide, civamide, olvanil, Nb-VNA, Nv-VNA, SB-705498, or anandamide.

In certain embodiments, the antagonist includes any known antagonist. In various embodiments, the antagonist is a TRPV1 antagonist including capsazepine, BCTC, IodoRTX, JYL-827, AMG9810, SB-705498, Aprepitant, Lanpepitant, CP-99,994, SDZ NKT 343, Ezlopitant, CP-96345, CP-99994, CP-122721, MK-869, GR 205171. RP 67580, Dapitant, Lanepitant, Noloitanium, Sarefutant, Casopitant, or Vestipitant.

It is contemplated that various chemical equivalents or other lachrymatory agents are also useful in the present invention. For example, it is contemplated that formulations comprising piperine, iso-piperine, chavicine, iso-chavicine, zingerone, hot pepper oil, hot pepper extract, and mixtures thereof are useful in the compositions of the present invention.

For a non-lethal temporarily incapacitating spray, the target should exhibit immediate closing of the eyes, shortness of breath, and burning sensation of the skin wherein the amount of time to recover from such symptoms is reduced by the addition of the antagonist. However, the composition of the invention should not be so strong that it produces excessive redness of the skin and lengthy inflammation requiring a recovery time of more than one hour.

Concentrations of TRPV1 agonist between 0.5% and 1.6% are preferred. Within this range, concentrations of 0.5% to 1.00% have been found to be useful for many self-defense applications in that they are stable and consistent in their performance, with the concentration of 1.00% exhibiting 90% to 95% effectiveness. It is known that a level of capsaicin of 1.45% is the most potent level that can be delivered without potential hazards. This is particularly important for law enforcement and military applications since there is a small population of individuals for which 0.90% concentration does not achieve proper inflammation, but at 1.45% all subjects achieve proper inflammation.

Concentrations of TRPV1 antagonist between 0.1% and 10.0% are preferred. Within this range, the invention provides the following concentrations: concentrations of 0.2% to 1.0%, 1.0% to 2.0%, 2.0% to 3.0%, 3.0% to 5.0%, or 5.0% to 10.0%.

Solvent System

The principle solvent for the formulations of the present invention is water. Additional chemicals in the present formulation include surfactants, sticking agents, preservatives or biocidal agents, coloring dyes or agents, fragrance, etc.

In certain embodiments, the formulation of the present invention contains mineral oil or other food grade oil. In certain embodiments, the concentration of food grade oil in the aqueous solution is about 1%, or more or less. In certain embodiments, the concentration of food grade oil in the aqueous solution is about 0.1% to about 99%, or more or less. In certain embodiments, the concentration of food grade oil in the aqueous solution is about 10%, or more or less. In certain embodiments, the concentration of food grade oil in the aqueous solution is about 50%, or more or less.

Mineral or other food grade oil has been found to be a useful additive to the present invention. Use of mineral oil in the formulation enhances dispersion, reduces fogging or misting of a potentially irritating or noxious odor. Mineral oil is non-toxic to humans, and is safe to use in households and other animal and people environments. The inert carrier oil added to the composition of the invention can be a combination of one or more inert carrier oils selected from the group consisting of mineral oil, organic oils, animal and vegetable oils, castor oil, hydrocarbon oils, and paraffinic oils.

In certain embodiments, the composition of the invention is contacted with a solvent system. The solvent system of the present invention has several physical and chemical properties that make this product significantly more stable and suitable for use for a broad range of applications. Furthermore, the solvent system of the present invention is non-toxic, non-carcinogenic, has a wide operating temperature range throughout which it maintains its stability. Also the solvent system readily dissolves and solubilizes oil based active ingredients while remaining non-flammable and without becoming corrosive to the environment or to people or animals. The solvent system is safe for skin contact and in fact can be used with pharmaceutical and skin care preparations. Additionally, when used in an aerosol or spray formulation, its unique characteristics produce more stable aerosol or other type of spray, that is controllable in rainy and windy conditions and less likely to contribute to prolonged airborne contamination or blow back due to windy conditions.

In particular, the solvent system has a significantly greater average molecular weight of 470 mw in comparison to the prior art solvents including water (MW 18.02) or isopropyl alcohol (MW 60). The solvent system also has a significantly lower vapor pressure of 0.0075 mmHg (70° F.) in comparison with water at 18.96 mmHg and isopropyl alcohol at 33 mmHg This unique combination of various physical and chemical factors in the solvent reduces the possibility of airborne chemical to vaporize eliminating the possibility of contamination of indoor area or bystanders resulting in a stable chemical during aerosol application in windy conditions, with minimal possibility of chemical blow back on user.

In certain embodiments, the solvent system of the present invention comprises a mixture of propylene glycol esters of short chain fatty acids and glycerol tris 2-ethylhexanoate.

Propylene glycol esters of short chain fatty acids are the propylene glycol mono- and diesters of caproic, capric, caprylic and lauric acid and their mixtures, including for example propylene glycol dicaprylate/dicaprate is a commonly used mixture of the propylene glycol diesters of caprylic (C8) and capric (C10) acids. They are very similar to other propylene glycol esters of fatty acids and to their triglycerides. These materials are neutral, nearly colorless and odorless esters with very low cloud points.

The propylene glycol esters of short chain fatty acids component used in the present invention is preferably propylene glycol dicaprylate/caprate. Propylene glycol dicaprylate/caprate is a mixture of the propylene glycol diester of caprylic acid and the ester of capric acid. The propylene glycol dicaprylate/caprate is a liquid with a boiling point greater than 200° C., a cloud point of −40° C., a flash point of 185° C. and a vapor pressure less than 1 hPa at 20° C. The density is 920 kg/m3 and the viscosity is 10 m Pa.s.

The glycerol tris 2-ethylhexanoate component is also known as trioctanoin. Glycerol tris 2-ethylhexanoate is the triester of glycerin and 2-ethylhexanoic acid. Glycerol tris-2-ethylhexahoate has similar properties, with a slightly higher flash point of 200° C., a slightly higher density of 950 kg/m3 and a much greater viscosity of 30 m Pa.s.

In the solvent system, the ratio of propylene glycerol dicaprylate/caprate to glycerol tris/2-ethylhexanoate is preferably in a range from about 20:80 to 80:20; and more preferably in a range from about 45:55 to about 55:45 by weight. In the most preferred embodiment of the present invention, the two components of the solvent system are present in about equal amounts by weight. If these ratio falls beyond the mentioned range the solvent may either freeze due to change in freezing point, become flammable due to change in flash point, or not remain stable in windy condition due to change in vapor pressure and surface tension.

The solvent system of the present invention was developed to withstand an extreme range of operating conditions. It has a cloud point (temperature where the solvent begins to turn cloudy) of −42° C. and a flashpoint of 205° C. This falls well within the non-flammable range for aerosol and spray type applications, even under extreme operating conditions.

The solvent system of the present invention is environmentally safe and readily biodegradable. Testing undertaken has shown that the solvent will undergo rapid and extensive biodegradation in the environment.

Many of the prior art solvent systems also exhibited problems in dissolving, or even suspending, the resinous active ingredients of the pepper spray composition and often requiring excessive agitation for lengthy periods of time. For example, the resinous active ingredients are non-soluble in a water based system. Not only must excess and vigorous mixing be undertaken, but other solvents must be added to permit even a limited degree of solubility. Although soluble in alcohol, no trace of water can be present, otherwise separation will occur.

In direct contrast, the solvent system of the present invention exhibits a high degree of oil solubility enabling it to solubilize most oily substances at both low and higher concentrations, i.e. from about 0.05% to about 30% by weight of an oil based active ingredient is readily solubilized in the novel solvent of the present invention. For example, oleoresin capsicum rapidly dissolves with minimal agitation and becomes a homogeneous part of the solvent system.

Propellant

Various propellants can be mixed with the solvent or formulation in order to place it under pressure so that the solvent or formulation can be dispensed as a spray. Any suitable propellant known to one of skill in the art can be used and will depend upon the particular application, the environmental effects the pressurized container will be subjected to, the size of the container, the desired range, and the like. The propellant should be able to maintain an adequate pressure and avoid over-pressurization at the desired operating temperature range.

Some propellants can vary their pressure in response to a change in the temperature. For example, isobutane and propane increase in pressure with an increase in temperature and nitrogen decreases in pressure as the temperature drops. Although these propellants can be used, care must be taken. If such an aerosol is stored inside a car during hot seasons the internal pressure can rise to cause deformation of the canister body and bursting. On the other hand when temperature fall during the cold season, the aerosol may lose its delivery range due to loss of pressure.

A particularly preferred propellant is carbon dioxide ($CO_2$) due to its highly desirable properties. $CO_2$ is colorless, odorless and noncombustible, and its pressure remains relatively unaffected by extreme temperatures. Furthermore, $CO_2$ evaporates instantly upon contact with the environment outside the spray device as it exits the valve opening or nozzle orifice. Thus, $CO_2$ simply created initial propulsion to launch the liquid formulation to the target and does not travel with the solvents to the target. This avoids the need to consider the effects of the propellant on the intended target or recipient of the spray.

Another propellant suitable for wide range of operating temperatures is nitrous oxide and is desirable for the same reasons as carbon dioxide.

The propellants can be used in any amount known to one of skill in the art to be suitable for pressurizing the solvent. In a preferred embodiment of the present invention, the propellant is present in an amount between 1 to 30% by weight as a pressurizing agent in the solvent resulting in a stable environment with none or minimal loss of pressure. For example, a starting pressure of 120 psi requires the use of about 4 to 5% $CO_2$ by weight to be introduced into the container holding the solvent mixture.

Although nitrogen is not suitable for small aerosol containers due to its loss of pressure with each spray and a concomitant decrease in the range with each spray, it is suitable for use with other pressurized delivery systems and in large pressurized systems.

The solvent system can also be used in other delivery systems such as fire extinguisher size canisters, larger pressurized tanks, ammunition capable of delivery of chemical payloads, paint pellet guns, vehicles capable of delivering chemicals and aircraft capable of chemical dissemination from air with any necessary and appropriate propellant or pressurizing agent.

Accordingly, one of skill in the art would be able to readily determine the appropriate propellant or pressurization agent for use with the solvent depending upon the desired application, the desired range, the active ingredient, the size of the container, the operating conditions, and the other factors influencing choice of propellant that one of skill in the art is familiar with.

In certain embodiments, the invention provides the composition of the invention, and other additives, including Tween 80, benzyl alcohol, isopropyl alcohol, and citric acid. In certain embodiments, these ingredients are combined in the following weight percent ratios relative to the entire lachrymator aerosol formulation: about 0.5-6.0 wt % TRPV1 agonist and antagonist; about 2-10 wt % Tween 80; about 1-5 wt % benzyl alcohol; and about 25-45 wt % isopropyl alcohol.

The propellant component preferably comprises about 2-6 wt % sodium bicarbonate and about 30-45 wt % water. Preferred formulations further comprise an aliquot of equal parts water and isopropanol to purge the dip tube inside the aerosol container after charging the container with the lachrymator component and the propellant component.

The lachrymator component and the propellant generating component are combined and packaged in a sealed aerosol container. When the two components of the propellant mixture are combined the mixture releases $CO_2$, which pressurizes the contents of the aerosol container and acts as the propellant gas.

The propellant mixture is formulated with the lachrymator component according to a variety of methods. In the preferred method, the aerosol container is first charged with the lachrymator component, which contains the citric acid/isopropanol combination, and the valve is crimped onto the container; the aqueous sodium bicarbonate solution is then charged to the vessel through the valve stem; the valve dip tube is then purged with an aliquot of equal parts water/isopropanol; and the valve actuator is attached.

It is contemplated that the order of addition of the citric acid and sodium bicarbonate components may be reversed by adding a citric acid/isopropanol aliquot to the container after combining the lachrymator/carrier component and the aqueous sodium bicarbonate component. This then would be followed by purging the dip tube with the water/IPA component as needed.

The foregoing mixtures are combined and packaged according to various methods for preparing and packaging aerosol formulations as is known in the art.

Self-Defense Device

Self-defense devices cover a wide range of threatening situations and are, by manufacture, individually suited to cover various sectors within a parameter space defined by axes such as lethality, level of user training, size and portability, ease of concealment, safety, accuracy and range of fire, ammunition storage capacity, and others. This specialization makes some devices more suitable for professional security personnel and others more suitable for personal use by civilians. The category of self-defense devices for personal use is characterized by low levels of lethality and requisite user training, small size and easy concealment, high safety levels, and poor-to-medium accuracy and range of fire. In addition, the possibility of facile one-handed operation is a definite advantage for such a device.

Self-defense devices contemplated for use by the invention include the following.

One self-defense device is a spray canister, which offers the potential victim a way of disabling a potential assailant. U.S. Pat. No. 5,219,096 discloses a squirt gun in handgun form in which the projection force and fluid storage are combined in a collapsible bulb forming the butt of the pistol.

While the overall size of a personal civilian self-defense device must be relatively small, the section of the device containing the active ammunition should be as capacious as possible within this constraint. Many of the devices disclosed in the above patents do not provide enough capacity for repeated discharges of the device as necessary to repel an assailant, particularly in situations in which the initial discharge misses the mark, or in situations in which several assailants are present.

Outside of the realm of devices specifically designed for self-defense purposes, there are a number of devices for containing and dispensing fluids that may be adaptable to a defense use when filled with a sufficiently noxious substance. U.S. Pat. No. 3,255,933 discloses a dispensing container with bellows, composed of rigid and flexible parts such that the compression of the bellows section provides a predictable and constant amount of pressurization of the contents of the container. U.S. Pat. No. 4,024,992 discloses an air atomizer bottle sprayer having a screw cap. U.S. Pat. No. 5,328,060 discloses a pack for free-flowing filler of a fluid or powdered nature.

It would be quite advantageous to have a fluid-ejecting self-defense device that overcomes the drawbacks of known self-defense and fluid dispensing devices, and is uniquely adapted to the operational parameters of personal civilian self-defense, specifically, low levels of lethality and user training, small size and ease of concealment, very high safety levels, and reasonable accuracy and range of fire. It would be of further advantage for the operation of such a device to be intuitive, easy, and preferably one-handed, even under stress.

Attack deterrent devices of the type that emit a repellent spray have been disclosed for use in personal protection. U.S. Pat. No. 5,088,624 provides a device that includes a housing that contains one or more canisters containing a noxious chemical, an irritant such as mace and/or an indelible dye for later identification of an assailant. Although the canisters afford great flexibility in the type of anti-assault spray that can be used, the housing of the '624 patent's device is relatively large, on the order of seven centimeters or more, and the device is therefore relatively unwieldy to carry on one's person.

Finger rings which contain a repellent that can be discharged at an attacker have also been known for use in the field of personal protection. U.S. Pat. Nos. 3,353,749, 4,061,249, and 4,135,645 all disclose rings which contain repellent sprays for discharge at an attacker. These rings are generally advantageous in that they conceal from an assailant the fact that the ring wearer is armed with repellent spray so that such assailant cannot disarm the ring wearer.

In other embodiments, the device includes a canister for containing a pressurized repellent such as the composition of the invention. The canister can be discharged in a directed spray to deter attack by a person or animal. The canister is relatively small, preferably four centimeters or less in its largest dimension, and thus is readily concealed. Also, the canister can include a clip for removably attaching the canister to an article worn or carried by a person. In addition, the canister can include a valve configured to discharge a limited amount of repellent in each activation of the valve to allow the user several opportunities to disable an attacker.

As an additional option for concealing the canister, the apparatus can include a finger ring to which the canister can be removably fixed. In a preferred configuration, the ring defines a cavity into which the canister can be removably inserted. In one embodiment, the apparatus can include a lever which has an end that engages with the canister's valve and a central portion that contacts a fulcrum defined in the ring, and which can be readily discharged when desired by squeezing an end of the lever toward the ring between two digits of the user's hand. In various embodiments of the canister as disclosed herein, the canister can include various safety mechanisms to prevent accidental discharge of the repellent. In addition, the apparatus can include a spray cap to redirect the repellent spray in a desired direction, and a ball valve that can be used to fill or refill the canister.

In certain embodiments, the invention provides a self-defense device that ejects an aimed stream or spray of fluid. The device is designed and constructed to be extremely safe to carry and use, intuitively comfortable in fitting the user's hand, capable of forcibly ejecting a significant amount of noxious fluid to a target at a range of 12 to 16 feet, and well-protected against accidental discharge.

The fluid-filled chamber is composed of two elements, a rigid section which faces the user at the time of discharge, and a flexible section which faces outwards towards a potential threat. The visual and tactile difference between these components of the chamber gives a powerful cue-to the user, making it nearly impossible to accidentally aim the device backwards at the user.

The phrase "differing tactile properties", when used within this specification and subsequent claims, refers to substantial differences in properties such as hardness, roughness, stickiness, specific gravity, and/or texture, that can be sensed when grasping an object. The device is preferably designed such that the two elements of the chamber have strongly differing tactile properties. This feature is critical to the proper use of the device under stress, in dark areas, and under severe time pressure.

The rigid section is designed to fit into the lower palm of the hand and to butt securely against the base of the user's thumb. The flexible section is contoured to the inner contours of the fingers.

The rigid section provides protection from accidental pressurizing of the contents of the chamber when the device is not in use, and therefore includes all sections of the chamber besides those necessary for pressurizing. The rigid section covers a substantial portion of the sides of the device, protecting against over-pressurizing of the chamber if pressure is applied from the sides, as would occur if the device were stepped upon. The flexible section of the chamber is configured to displace a significant amount of the contents of the chamber without entirely emptying it on the first discharge.

A further adaptation to the operational needs of the civilian self-defense user is the safety valve. This valve is part of the ejection assembly and when closed, positively prevents ejection of the noxious fluid. This valve is operable by thumb pressure without changing the grip on the device, or using the opposite hand. The valve is placed to naturally engage the thumb of the user, such that the user can carry the device comfortably in a position that affords rapid release of the safety and discharge of the device as needed.

In certain embodiments, the device is a self-defense device including a chamber with a rigid outer wall section, and a flexible outer wall section attached to the rigid outer wall section, an ejection assembly fixed inside and extending through the outer wall of the chamber which includes a tube extending through the chamber, and fluidly communicating therewith, and a nozzle attached to an upward end of the tube and extending through the chamber, and a noxious fluid disposed within the chamber; wherein the chamber is designed and constructed so as to be completely filled by the fluid, and in which external pressure exerted upon the flexible outer wall section increases the internal pressure of the chamber, such that the fluid is forcefully ejected out of the device through the ejection assembly and out of the nozzle.

In certain embodiments, the device is a directional self-defense device including a chamber including a rigid outer wall section, and a flexible outer wall section attached to the rigid outer wall section, an ejection assembly fixed inside and communicating through the outer wall of the chamber, the ejection assembly including a tube extending through the chamber, and fluidly communicating therewith, a nozzle attached to an upward end of the tube and extending through the chamber, and a noxious fluid filling the chamber built so that external pressure exerted upon the flexible outer wall section increases an internal pressure of the chamber, such that the fluid is forcefully ejected out of the device through the ejection assembly and out of the nozzle, and wherein the rigid section and the flexible section have differing tactile properties so as to be easily distinguishable by a user.

In certain embodiments, the invention also specifies a method of self defense, including the following steps: providing a self-defense device including a chamber including a rigid outer wall section, and a flexible outer wall section attached to the rigid outer wall section, and an ejection assembly fixed inside and extending through the outer wall of the chamber, the ejection assembly including a tube extending through the chamber, and fluidly communicating therewith, and a nozzle attached to an upward end of the tube and extending through the chamber, and a noxious fluid completely filling the chamber; then grasping the self-defense device with the rigid chamber section butted against the palm of the hand and the base of the thumb, and the flexible chamber section held within loosely closed fingers; then aiming the device at a target, and squeezing the flexible chamber section of the device, so as to forcefully and directedly eject the noxious fluid at the target through the nozzle.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Materials

Capsaicin was from Sigma (St. Louis, Mo., USA); BCTC was obtained from Biomol (Plymouth Meeting, Pa.); 5' Iodo-RTX was from LC Laboratories (Woburn, Mass., USA); AMG 9810 was purchased from Tocris Bioscience (Ellisville, Mo., USA); JYL-827 and Capsazepine were obtained from Axxora, LLC (San Diego, Calif., USA)

Cell Culture

The stable CHO cell clone expressing rTRPV1 (Tet-Off) was the generous gift of James E. Krause and Daniel N. Cortwright (Neurogen Corp., Branford, Conn., USA). These cells were cultured in maintaining medium (HAM F-12 supplemented with 10% FBS (USA sourced, Atlanta biologicals, Lawrenceville, Ga., USA), 25 mM HEPES, pH 7.5, 250 µg/ml geneticin (F-12, HEPES, and geneticin are from Invitrogen, Carlsbad, Calif., USA) and 1 mg/L tetracycline (Calbiochem, La Jolla, Calif., USA).

Intracellular $Ca^{2+}$ Imaging

CHO-rTRPV1 cells were seeded on 25 mm round glass coverslips in 35×10 mm tissue culture dishes in maintaining medium. After 24 hours, the medium was replaced with inducing medium (maintaining medium without geneticin and tetracycline, but containing 1 mM sodium butyrate) to induce TRPV1 expression. Experiments were performed approximately 24 hours after induction. For fura-2 AM (Invitrogen, Carlsbad, Calif., USA) loading, the cells were incubated in DPBS containing calcium and magnesium (Invitrogen, Carlsbad, Calif., USA), 0.5 mg/ml BSA (Sigma, St. Louis, Mo., USA), and 5 µM Fura-2 AM for 2 hours in the dark at 20° C. After 2 hours, the loaded cells were washed 2× with DPBS without calcium and magnesium and immersed in maintaining medium until the measurements. The measurements were carried out in DPBS containing calcium and magnesium, plus 0.5 mg/ml BSA. The fluorescence of individual cells treated simultaneously with a single dose of agonist and antagonist was measured with an InCyt Im2 fluorescence imaging system (Intracellular Imaging, Cincinnati, Ohio, USA). The cells within the selected field were illuminated alternately at 340 and 380 nm. Emitted light >510 nm was measured. To determine the approximate intracellular $Ca^{2+}$ concentrations, the system was calibrated using a fura-2 calibration kit (Invitrogen, Carlsbad, Calif., USA). Data were analyzed with the Incyt software and tabulated with Microsoft Excel spreadsheet and graphed with Origin 6.0 (OriginLab Corp., Northhampton, Mass., USA) software.

Determination of Inhibition Values

The TRPV1 agonist and antagonist were added simultaneously to fura-2 AM loaded CHO-rTRPV1 cells after 90 seconds from the beginning of the measurement (baseline) and monitored continuously for an additional 10 minutes. Inhibition values were compared to the maximally effective dose of capsaicin (300 nM) in the same experiment (see FIGS. 2A-2E) or to the indicated concentration of capsaicin (see FIGS. 3A-3E). Experiments were performed three times, each on different days with approximately 30-49 cells measured.

Incorporation by Reference

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Equivalents Those skilled in the art will recognize, or be able to ascertain using no more than routine experimentation, many equivalents of the specific embodiments of the invention described herein. Such equivalents are intended with be encompassed by the following claims.

What is claimed:

1. A method for incapacitating a mammal, comprising:
   (a) providing a non-lethal temporarily incapacitating composition suitable for use in an aerosol or spray application, the incapacitating formulation comprising an effective amount of a TRPV1 agonist, an effective amount of a TRPV1 antagonist, and a solvent system;
   (b) applying the non-lethal temporarily incapacitating formulation to the mammal, wherein the agonist and antagonist are administered simultaneously to the mammal; and
   (c) temporarily incapacitating the mammal,
   wherein the amount of antagonist does not decrease a maximal response to agonist by more than 20%, compared to agonist alone, at time 0, and the amount of antagonist reduces the response to agonist by at least 80% at 20 minutes.

2. The method of claim 1, wherein the TRPV1 agonist is capsaicin, dibenzoxazepine (CR), oleoresin capscium (OC), oleoresin paprika, paprika, capsicums (chili peppers), trans-8-methyl N-vanillyl-6-nonenamide (capsaicin), 8-methyl-N-vanillyl-nonamide (dihydrocapsaicin), 7-methyl-N-vanillyl-octamide (nordihydrocapsaicin), 9-methyl-N-vanillyl-decamide (homodihydrocapsaicin), trans-9-methyl-N-vanillyl-7-decenamide (homocapsaicin), (3R, 3, 5 R)-3,3'-dihydroxy-a,k-caroten-6-one (capsanthin), N-vanillyl-octamide, N-vanillyl-nonamide, N-vanillyl-decanamide, N-vanillyl-undecanamide, N-vanillyl-paaiperic acid amide, nonivamide, civamide, olvanil, Nb-VNA, Nv-VNA, SB-705498, or anadamide.

3. The method of claim 2, wherein the TRPV1 agonist is capsaicin.

4. The method of claim 1, wherein the TRPV1 antagonist is BCTC, IodoRTX, JYL-827, AMG9810, or capsazepine, SB-705498, Aprepitant, Lanpepitant, CP-99,994, SDZ NKT 343, Ezlopitant, CP-96345, CP-99994, CP-122721, MK-869, GR 205171. RP 67580, Dapitant, Lanepitant, Noloitanium, Sarefutant, Casopitant, or Vestipitant.

5. The method of claim 4, wherein the TRPV1 antagonist is BCTC, IodoRTX, JYL-827, AMG9810, or capsazepine.

6. The method of claim 1 wherein the solvent system comprises approximately equal amounts of the propylene glycol dicaprylate/caprate and glycerol tris (2-ethylhexanoate).

7. The method of claim 1 wherein said applying comprises spraying the non-lethal temporarily incapacitating formulation into the eyes of the subject.

8. The method of claim 1, wherein the non-lethal temporarily incapacitating composition further comprises a propellant.

9. The method of claim 8 wherein said propellant is miscible in said solvent system.

10. The method of claim 9 wherein said propellant is carbon dioxide.

11. The method of claim 1, wherein the TRPV1 agonist is antagonized by 80% by the TRPV1 antagonist in between 1 minute and 20 minutes.

12. The method of claim 11, wherein the TRPV1 agonist is antagonized by 80% by the TRPV1 antagonist in between 1 minute and 5 minutes.

13. The method of claim 1, wherein the TRPV1 agonist and TRPV1 antagonist are present in an amount of about 0.01% to about 5% by weight of the solvent system.

14. The method of claim 13, wherein the TRPV1 agonist and TRPV1 antagonist are present in an amount of 0.1% to about 3% by weight of the solvent system.

15. The method of claim 1, wherein said incapacitating composition is formulated to cause, upon application of the system to the facial area of a recipient, inflammation to the facial area of the recipient.

16. The method of claim 1, wherein said application of the composition into the facial area of the subject causes the subject to experience a symptom selected from the group consisting of immediate closing of the eyes, shortness of breath, and burning sensation.

17. The method of claim 16, wherein the symptom lasts from 1 minute to 45 minutes.

18. The method of claim 1, wherein the TRPV1 agonist and TRPV1 antagonist are present in a ratio of 300:1, 30:1, 10:1, 3:1, 1:1, 3:10, 1:10, 1:20, or 3:100.

19. The method of claim 4, wherein the TRPV1 antagonist is BCTC or IodoRTX.

20. The method of claim 1, wherein the TRPV1 agonist exhibits a rate of penetration that is faster than the TRPV1 antagonist rate of penetration.

* * * * *